(12) United States Patent
Mathias et al.

(10) Patent No.: US 7,824,343 B2
(45) Date of Patent: *Nov. 2, 2010

(54) METHOD AND APPARATUS FOR BLOOD SAMPLING

(75) Inventors: Jean-Marie Mathias, Lillois (BE); Bryan Blickhan, Zion, IL (US); Stephanie Haldiman, Cary, IL (US); Larry Servi, Jr., Hawthorn Woods, IL (US); Jean-Claude Bernes, Faimes (BE); Daniel F. Bischof, Bull Valley, IL (US)

(73) Assignee: Fenwal, Inc., Lake Zurich, IL (US)

( * ) Notice: Subject to any disclaimer, the term of this patent is extended or adjusted under 35 U.S.C. 154(b) by 976 days.

This patent is subject to a terminal disclaimer.

(21) Appl. No.: 10/956,296

(22) Filed: Oct. 1, 2004

(65) Prior Publication Data

US 2005/0148993 A1    Jul. 7, 2005

Related U.S. Application Data

(60) Continuation-in-part of application No. 10/304,299, filed on Nov. 26, 2002, now Pat. No. 7,044,941, which is a division of application No. 09/492,060, filed on Jan. 27, 2000, now Pat. No. 6,520,948, which is a continuation-in-part of application No. 09/364,628, filed on Jul. 29, 1999, now Pat. No. 6,387,086.

(51) Int. Cl.
  *A61B 5/00*   (2006.01)
  *A61B 19/00*  (2006.01)
  *B65D 81/00*  (2006.01)
  *A61M 37/00*  (2006.01)

(52) U.S. Cl. .............. 600/573; 600/578; 600/580; 604/6.15; 604/403; 604/408; 604/409; 604/410

(58) Field of Classification Search ............... 600/573, 600/578, 580; 604/6.15, 403, 408, 409, 410, 604/319
See application file for complete search history.

(56) References Cited

U.S. PATENT DOCUMENTS

| | | | |
|---|---|---|---|
| 2,469,641 A | 2/1949 | Kleiner | |
| 2,950,716 A * | 8/1960 | Walter et al. | ............... 604/409 |
| 2,955,595 A | 10/1960 | Semple | ..................... 128/214 |
| 3,064,647 A | 11/1962 | Earl | |
| 3,127,892 A | 4/1964 | Bellamy, Jr. et al. | |

(Continued)

FOREIGN PATENT DOCUMENTS

CN        2301263 Y      12/1998

(Continued)

OTHER PUBLICATIONS

Thomas Gibson & Walter Norris, "Skin Fragments Removed by Injection Needles," *The Lancet*, (1958), vol. 8, p. 983-985.

(Continued)

*Primary Examiner*—Max Hindenburg
*Assistant Examiner*—Jeffrey G Hoekstra
(74) *Attorney, Agent, or Firm*—Cook Alex Ltd.

(57) ABSTRACT

Methods and apparatus for collecting blood samples in vacuum sample tubes are disclosed. The samples, including the initial blood sample, are substantially free of excess air.

10 Claims, 15 Drawing Sheets

U.S. PATENT DOCUMENTS

| | | | |
|---|---|---|---|
| 3,187,750 A | 6/1965 | Tenczar | 128/272 |
| 3,217,710 A | 11/1965 | Beall et al. | |
| 3,342,179 A | 9/1967 | Ellmann | |
| 3,416,528 A | 12/1968 | Kahn | |
| 3,467,095 A | 9/1969 | Ross | 128/214.2 |
| 3,469,572 A | 9/1969 | Nehring | |
| 3,494,352 A | 2/1970 | Russo et al. | |
| 3,654,924 A | 4/1972 | Wilson et al. | 128/214 |
| 3,817,240 A | 6/1974 | Ayres | |
| 3,890,203 A | 6/1975 | Mehl | |
| 3,931,815 A | 1/1976 | Takatusuki | |
| 3,945,380 A | 3/1976 | Dabney et al. | 128/214 |
| 4,007,738 A | 2/1977 | Yoshino | |
| 4,056,101 A | 11/1977 | Geissler et al. | 128/214 |
| 4,121,585 A | 10/1978 | Becker, Jr. | |
| 4,140,108 A | 2/1979 | Nugent | |
| 4,181,140 A | 1/1980 | Bayham et al. | |
| 4,195,632 A | 4/1980 | Parker et al. | |
| 4,197,847 A | 4/1980 | Djerassi | 128/214 |
| 4,212,308 A | 7/1980 | Percarpio | |
| 4,253,458 A | 3/1981 | Bacehowski et al. | |
| 4,256,120 A | 3/1981 | Finley | |
| 4,270,534 A | 6/1981 | Adams | |
| 4,294,247 A | 10/1981 | Carter et al. | |
| 4,295,477 A | 10/1981 | Christinger | |
| 4,296,759 A | 10/1981 | Joslin et al. | |
| 4,307,731 A | 12/1981 | Kaufman | |
| 4,320,769 A | 3/1982 | Eichhorn et al. | |
| 4,325,369 A | 4/1982 | Nilson | |
| 4,340,049 A | 7/1982 | Munsch | |
| 4,386,622 A | 6/1983 | Munsch | |
| 4,407,660 A | 10/1983 | Nevens et al. | 604/6 |
| 4,441,951 A | 4/1984 | Christinger | |
| 4,507,123 A | 3/1985 | Yoshida | 604/408 |
| 4,547,186 A | 10/1985 | Bartlett | |
| 4,586,928 A | 5/1986 | Barnes et al. | |
| 4,637,934 A | 1/1987 | White | |
| 4,655,764 A | 4/1987 | Sato | |
| 4,658,655 A | 4/1987 | Kanno | |
| 4,670,013 A | 6/1987 | Barnes et al. | 604/403 |
| 4,687,474 A | 8/1987 | Takanashi | 604/257 |
| 4,763,648 A | 8/1988 | Wyatt | |
| 4,784,650 A | 11/1988 | Coburn | |
| 4,786,286 A | 11/1988 | Cerny et al. | 604/406 |
| 4,790,815 A | 12/1988 | Balteau et al. | |
| 4,804,363 A | 2/1989 | Valeri | 604/6 |
| 4,820,297 A | 4/1989 | Kaufman et al. | 604/409 |
| 4,846,795 A | 7/1989 | Minagawa | 604/410 |
| 4,865,583 A | 9/1989 | Tu | |
| 4,892,537 A | 1/1990 | Carmen et al. | |
| 4,900,321 A | 2/1990 | Kaufman et al. | 604/409 |
| 4,900,322 A | 2/1990 | Adams | 604/410 |
| 4,911,696 A | 3/1990 | Miyasaka et al. | 604/244 |
| 4,938,758 A | 7/1990 | Ali-Sioufi | |
| 4,943,283 A | 7/1990 | Hogan | |
| 4,976,708 A | 12/1990 | Oshiyama | |
| 4,991,601 A | 2/1991 | Kasai et al. | |
| 4,994,039 A | 2/1991 | Mattson | 604/408 |
| 5,002,066 A | 3/1991 | Simpson et al. | 128/760 |
| 5,033,476 A | 7/1991 | Kasai | |
| 5,045,067 A | 9/1991 | Ohnaka et al. | 604/244 |
| 5,046,509 A | 9/1991 | Kater | 128/764 |
| 5,048,537 A | 9/1991 | Messinger | |
| 5,061,365 A | 10/1991 | Utterberg | 210/90 |
| 5,061,451 A | 10/1991 | Ganshirt et al. | |
| 5,084,034 A | 1/1992 | Zanotti | |
| 5,098,371 A | 3/1992 | Juji et al. | 604/4 |
| 5,100,376 A | 3/1992 | Blake, III | |
| 5,102,407 A | 4/1992 | Carmen et al. | |
| RE33,924 E | 5/1992 | Valeri | 604/6 |
| 5,114,400 A | 5/1992 | Lynn | |
| 5,122,129 A | 6/1992 | Olson et al. | 604/905 |
| 5,123,570 A | 6/1992 | Dubow et al. | |
| 5,125,920 A | 6/1992 | Ishida | |
| 5,141,490 A | 8/1992 | Fujii et al. | 604/6 |
| 5,141,645 A | 8/1992 | Shiraki et al. | 210/513 |
| 5,154,716 A | 10/1992 | Bauman et al. | |
| 5,167,656 A | 12/1992 | Lynn | |
| 5,180,504 A | 1/1993 | Johnson et al. | 210/767 |
| 5,188,629 A | 2/1993 | Shimoda | |
| 5,259,841 A | 11/1993 | Hohendorf et al. | |
| 5,269,946 A | 12/1993 | Goldhaber et al. | 210/767 |
| 5,270,003 A | 12/1993 | Bernes et al. | |
| 5,300,060 A | 4/1994 | Nelson | 604/410 |
| 5,330,462 A | 7/1994 | Nakamura | 604/410 |
| 5,358,482 A | 10/1994 | Panzani | 604/6 |
| 5,360,012 A | 11/1994 | Ebara et al. | |
| 5,372,143 A | 12/1994 | Bernes et al. | |
| 5,395,347 A | 3/1995 | Blecher et al. | |
| 5,403,304 A | 4/1995 | Ishida | 604/403 |
| 5,417,681 A | 5/1995 | Miyake et al. | 604/410 |
| 5,431,174 A | 7/1995 | Knute | |
| 5,454,806 A | 10/1995 | Shinonome | 604/408 |
| 5,464,397 A | 11/1995 | Powers, Jr. | |
| 5,480,378 A | 1/1996 | Weis-Fogh et al. | 604/5 |
| 5,484,418 A | 1/1996 | Quiachon et al. | |
| 5,496,281 A | 3/1996 | Krebs | |
| 5,496,301 A | 3/1996 | Hlavinka et al. | |
| 5,505,716 A | 4/1996 | Simmet | |
| 5,512,187 A | 4/1996 | Buchholz et al. | 210/767 |
| 5,523,004 A | 6/1996 | Tanokura et al. | 210/782 |
| 5,527,472 A | 6/1996 | Bellotti et al. | 210/767 |
| 5,545,339 A | 8/1996 | Bormann et al. | |
| 5,573,526 A | 11/1996 | Hess | |
| 5,573,527 A | 11/1996 | Macabasco et al. | |
| 5,601,730 A | 2/1997 | Page et al. | |
| 5,620,008 A | 4/1997 | Shinar et al. | |
| 5,649,907 A | 7/1997 | Mori et al. | 604/85 |
| 5,665,074 A | 9/1997 | Kelly | |
| 5,685,875 A | 11/1997 | Hlavinka et al. | |
| 5,702,383 A | 12/1997 | Giesler et al. | 604/409 |
| 5,743,872 A | 4/1998 | Kelly | |
| RE35,804 E | 5/1998 | Stewart | 210/767 |
| 5,769,839 A | 6/1998 | Carmen et al. | 604/408 |
| 5,772,608 A | 6/1998 | Dhas | 600/578 |
| 5,772,880 A | 6/1998 | Lynn et al. | |
| RE35,841 E | 7/1998 | Frank et al. | |
| 5,776,338 A | 7/1998 | Mari | |
| 5,836,619 A | 11/1998 | Shemesh et al. | |
| 5,858,015 A | 1/1999 | Fini | |
| 5,879,318 A | 3/1999 | Van Der Heiden et al. | 604/6 |
| 5,885,261 A * | 3/1999 | Longo et al. | 604/319 |
| 5,897,526 A | 4/1999 | Vaillancourt | |
| 5,928,214 A | 7/1999 | Rubinstein et al. | 604/410 |
| 6,027,938 A | 2/2000 | Barnes et al. | |
| 6,051,136 A | 4/2000 | Mari | |
| 6,123,859 A | 9/2000 | Lee et al. | 210/767 |
| 6,126,618 A | 10/2000 | Bischof | |
| 6,132,413 A | 10/2000 | Mathias et al. | 604/403 |
| 6,159,192 A | 12/2000 | Fowles et al. | |
| 6,221,264 B1 | 4/2001 | Ishida et al. | |
| 6,234,538 B1 | 5/2001 | Lauer | 285/3 |
| 6,267,564 B1 | 7/2001 | Rapheal | |
| 6,267,745 B1 | 7/2001 | Mathias et al. | |
| 6,287,265 B1 | 9/2001 | Gleason | 600/573 |
| 6,325,775 B1 | 12/2001 | Thom et al. | |
| 6,328,726 B1 | 12/2001 | Ishida et al. | 604/408 |
| 6,344,139 B1 | 2/2002 | Utterberg | 210/232 |
| 6,358,420 B2 | 3/2002 | Blickhan et al. | 210/663 |
| 6,364,847 B1 | 4/2002 | Shulze et al. | 600/573 |
| 6,387,069 B1 | 5/2002 | Utterberg | 604/4.01 |
| 6,387,086 B2 | 5/2002 | Mathias et al. | |
| 6,488,860 B2 | 12/2002 | Mari et al. | 210/806 |
| 6,491,679 B1 | 12/2002 | Okamoto et al. | 604/410 |

| | | | |
|---|---|---|---|
| 6,495,039 B1 | 12/2002 | Lee et al. ............... 210/257.1 |
| 6,517,508 B1 | 2/2003 | Utterberg et al. ........... 604/4.01 |
| 6,520,948 B1 | 2/2003 | Mathias et al. |
| 6,585,875 B1 | 7/2003 | Ryabkov ................. 205/87 |
| 6,592,613 B1 | 7/2003 | Ishida et al. ............ 609/408 |
| 6,626,884 B1 | 9/2003 | Dillon et al. ............ 604/409 |
| 6,632,201 B1 | 10/2003 | Mathias et al. |
| 6,669,905 B1 | 12/2003 | Mathias et al. |
| 6,692,479 B2 | 2/2004 | Kraus et al. ............ 604/410 |
| 6,969,419 B1 | 11/2005 | Macemon |
| 6,997,893 B2 | 2/2006 | Mathias et al. |
| 7,044,941 B2 | 5/2006 | Mathias et al. |
| 2001/0025167 A1 | 9/2001 | Kraus et al. ............ 604/410 |
| 2001/0037078 A1 | 11/2001 | Lynn et al. |
| 2001/0052497 A1 | 12/2001 | Blickhan et al. ........... 210/669 |
| 2002/0019621 A1 | 2/2002 | Mathias et al. ............ 604/409 |
| 2002/0151834 A1 | 10/2002 | Utterberg ............... 604/6.16 |
| 2002/0183679 A1 | 12/2002 | Deverre ............... 604/6.15 |
| 2003/0144607 A1 | 7/2003 | Mathias et al. ............ 600/573 |
| 2003/0176813 A1 | 9/2003 | Mathias et al. ............ 600/576 |
| 2003/0208151 A1 | 11/2003 | Kraus et al. ............ 604/4.01 |
| 2004/0019344 A1 | 1/2004 | Peterson et al. ............ 604/411 |
| 2004/0082899 A1 | 4/2004 | Mathias et al. |
| 2004/0106890 A1 | 6/2004 | Goudaliez et al. |
| 2004/0260265 A1 | 12/2004 | Goudaliez et al. |
| 2005/0143712 A1 | 6/2005 | Mathias et al. |
| 2006/0111658 A1 | 5/2006 | Mathias et al. |
| 2006/0111687 A1 | 5/2006 | Mathias et al. |

FOREIGN PATENT DOCUMENTS

| | | | |
|---|---|---|---|
| DE | 20311868 U1 | 12/2003 |
| EP | 0 334 956 A1 | 10/1989 |
| EP | 0 356 002 A2 | 2/1990 |
| EP | 0 428 723 A1 | 5/1991 |
| EP | 0 455 215 A2 | 11/1991 |
| EP | 0 462 548 A1 | 12/1991 |
| EP | 0 357 863 B1 | 4/1993 |
| EP | 0 714 667 A2 | 6/1996 |
| EP | 1 064 959 A1 | 1/2004 |
| EP | 1498148 | 1/2005 |
| EP | 03 71 6592 | 2/2009 |
| FR | 1 586 087 | 2/1970 |
| FR | 2 655 532 A1 | 8/1991 |
| FR | 1320869 A | 2/2009 |
| JP | 10 211274 A | 8/1998 |
| WO | WO 89/04141 | 5/1989 |
| WO | WO 90/02515 | 3/1990 |
| WO | WO 96/17514 | 6/1996 |
| WO | WO 96/37150 | 11/1996 |
| WO | WO 97/41905 | 11/1997 |
| WO | WO 98/28057 | 7/1998 |
| WO | WO 99/36109 | 7/1999 |
| WO | WO 99/58094 | 11/1999 |
| WO | WO 00/06225 | 2/2000 |
| WO | WO 00/07642 | 2/2000 |
| WO | WO 00/24313 | 5/2000 |
| WO | PCT/US00/19076 | 10/2000 |
| WO | PCT/US2005/034504 | 5/2006 |

OTHER PUBLICATIONS

Morris Blajchman et al., "Bacteria in the Blood Supply: An Overlooked Issue in Transfusion Medicine," *Blood Safety and Current Challenges*, (1992), p. 213-228.

B.B. Barrett et al., "Strategies for the Avoidance of Bacterial Contamination of Blood Components," *Transfusion*, (1993), vol. 33, No. 3, p. 228-233.

P.I. Figueroa et al., "Distribution of Bacteria in Fluid Passing Through an Inoculated Collection Needle," *Transfusion Medicine*, (1995), vol. 35, suppl. 10, p. 11S, Abstract # S42.

A.M. Soeterboek et al., "Prevalence of Bacterial Contamination in Whole-Blood after Donation," *Vox Sanguinis*, (1995), vol. 69, p. 149.

H. Olthuis et al., "A Simple Method to Remove Contaminating Bacteria During Venepuncture," *Vox Sanguinis*, (1996), vol. 70, suppl. 2, p. 113, Abstract #1/2C-33 OP; Karger Medical and Scientific Publishers, Makuhari Messe, Japan.

C. Vassort-Bruneau, P. Perez et al., "New Collection System to Prevent Contamination with Skin Bacteria," *Transfusion Medicine: 25th Congress of International Society of Blood Transfusion*, (1996), vol. 74, suppl. 1, Abstract 1039; Karger Medical and Scientific Publishers, Oslo, Norway.

Claes Högman, "Serious Bacterial Complications from Blood Components—How Do They Occur?," *Transfusion Medicine*, (1998), vol. 8, p. 1-3.

C. Vassort, P. Allouch et al., "Efficacy of a Collection Procedure on Bacterial Contamination During Venous Puncture," *Transfus Clin Biol*, (1998), vol. 5, suppl. 1, Abstract 06-6.

Dirk de Korte et al., "Determination of the Degree of Bacterial Contamination of Whole-Blood Collections Using an Automated Microbe-Detection System," *Transfusion*, (2000), vol. 41, p. 815-818.

S.J. Wagner, D. Robinette, L.I. Friedman, & J. Miripol, "Diversion of Initial Blood Flow to prevent Whole-Blood Contamination by Skin Surface Bacteria: An In Vitro Model," *Transfusion*, (2000), vol. 40, p. 335-338.

M. Chassaigne, C. Vassort-Bruneau, P. Allouch, A. Audurier et al., "Reduction of Bacterial Load by Predonation Sampling," *Transfusion and Apheresis Science*, (2001), vol. 24, p. 253.

P. Perez et al., "Multivariate Analysis of Determinants of Bacterial Contamination of Whole-Blood Donations," *Vox Sanguinis*, (2001), vol. 82, p. 55-60.

Dirk de Korte et al. "Diversion of First Blood Volume Results in a Reduction of Bacterial Contamination for Whole-Blood Collections," *Vox Sanguinis*, (2002), vol. 83, p. 13-16.

Roger Dodd, "Bacterial Contamination of Blood Components," *American Red Cross*.

Haemonetics, *Introducing the MCS3P Multi-component System*, (1993). [Brochure].

Baxter, *Fenwal®: Access Closed System Apheresis Kit for Single Venous Access*, (1994).

Foi, *FDA 501(k) Filing for COBE Spectra Extended Life Platelet Set with Integrated Leukoreduction Filter*, (1995).

Baxter, Brochure for Amicus® Separator—Single Needle Draw (1996).

C.Rose et al., "Evaluation [of ] the MCS® + LN 9000 Continuous (In-Line) Leukoreduction Filter;" *Haemonetics Blood Services & Training Institute*, Tucson, Arizona.

Haemonetics, "Timing is Everything: Leukoreduction Your Platelets Before Storage." [Brochure].

Notice of Allowance mailed Nov. 9, 2009 in U.S. Appl. No. 11/251,283.

* cited by examiner

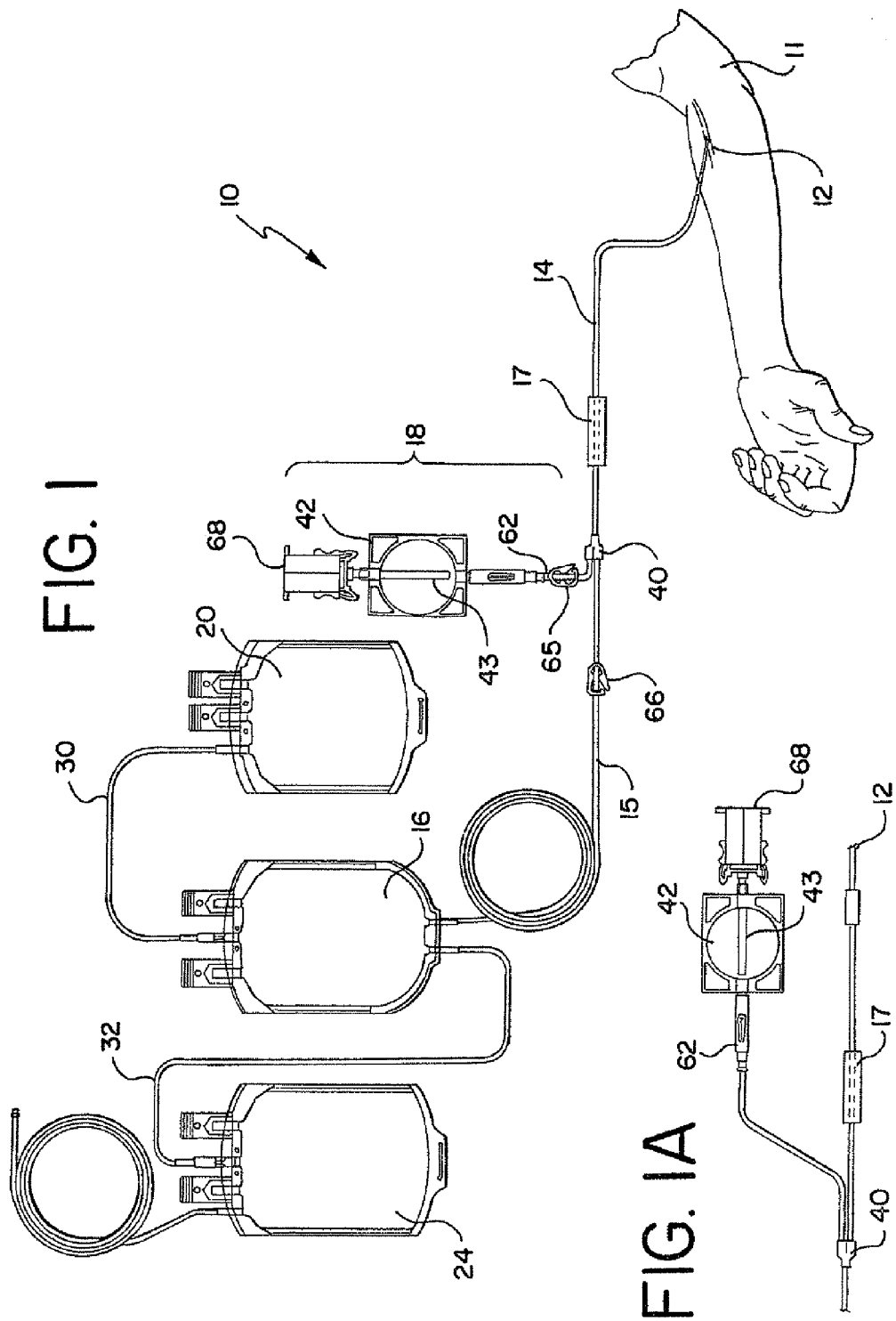

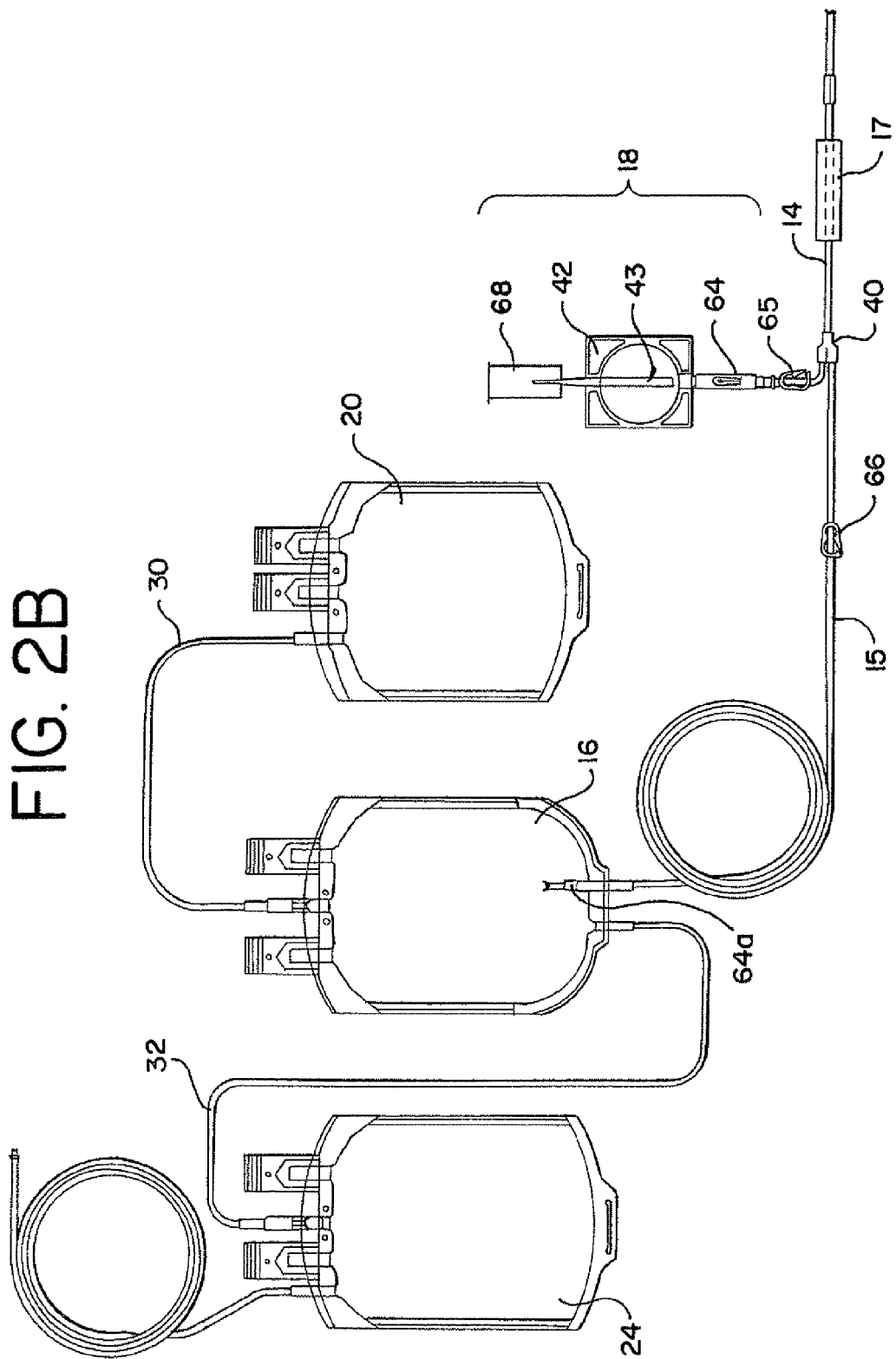

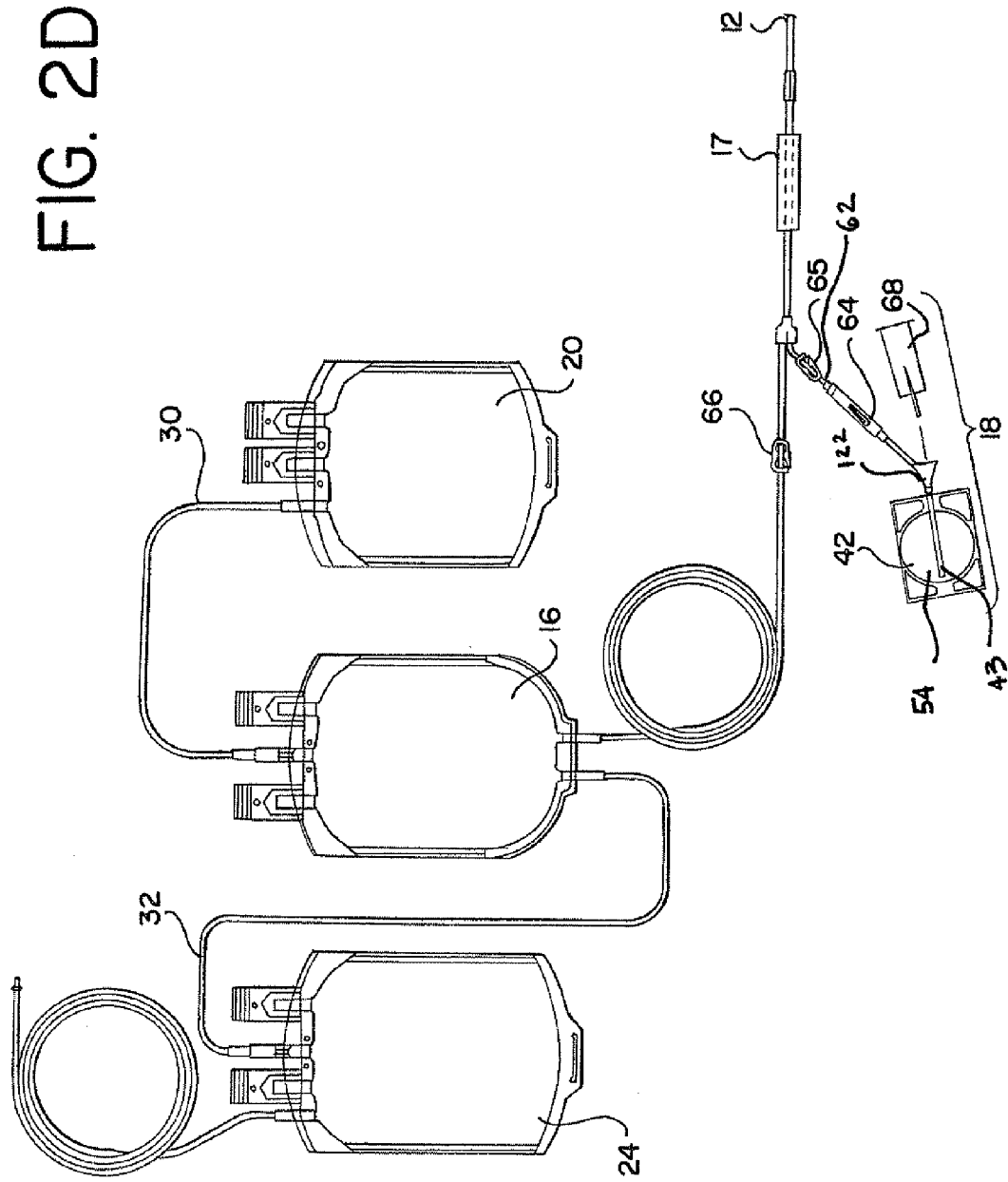

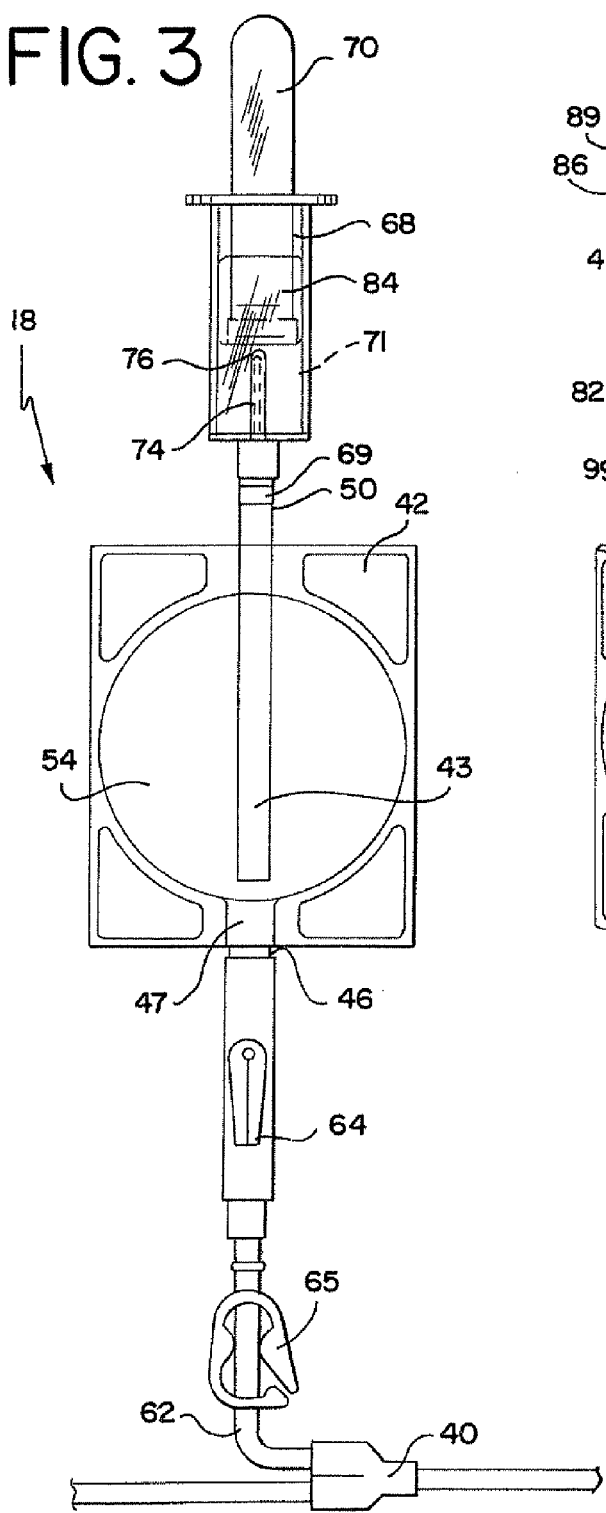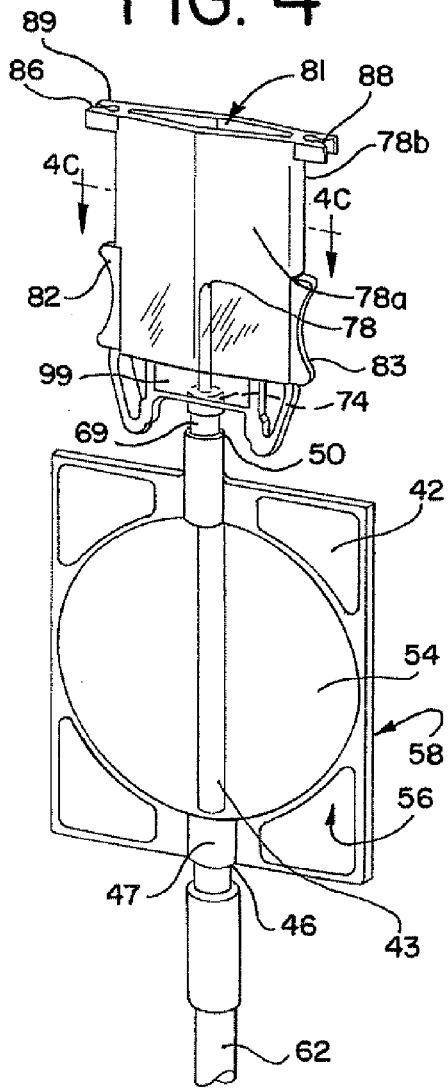

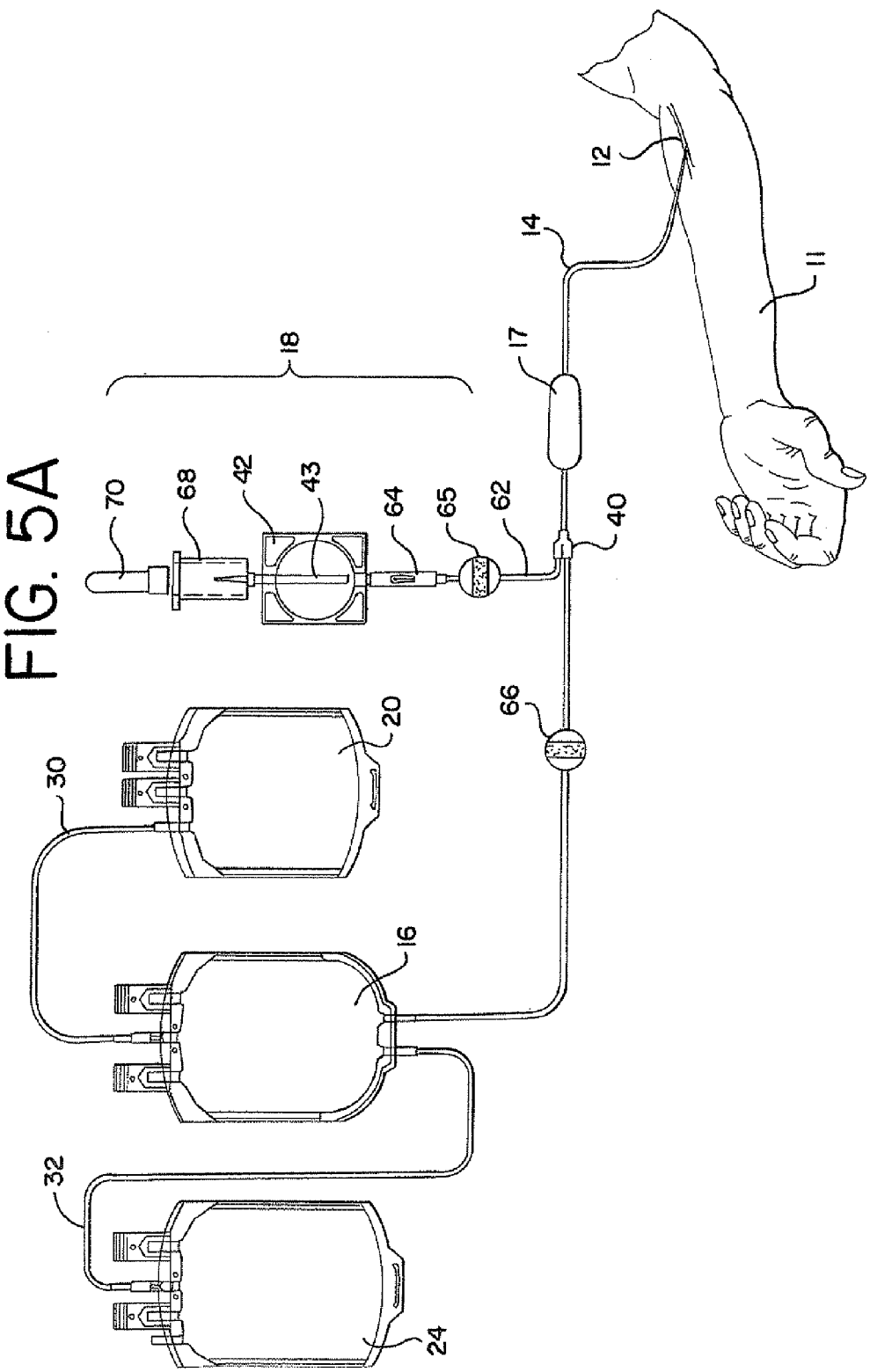

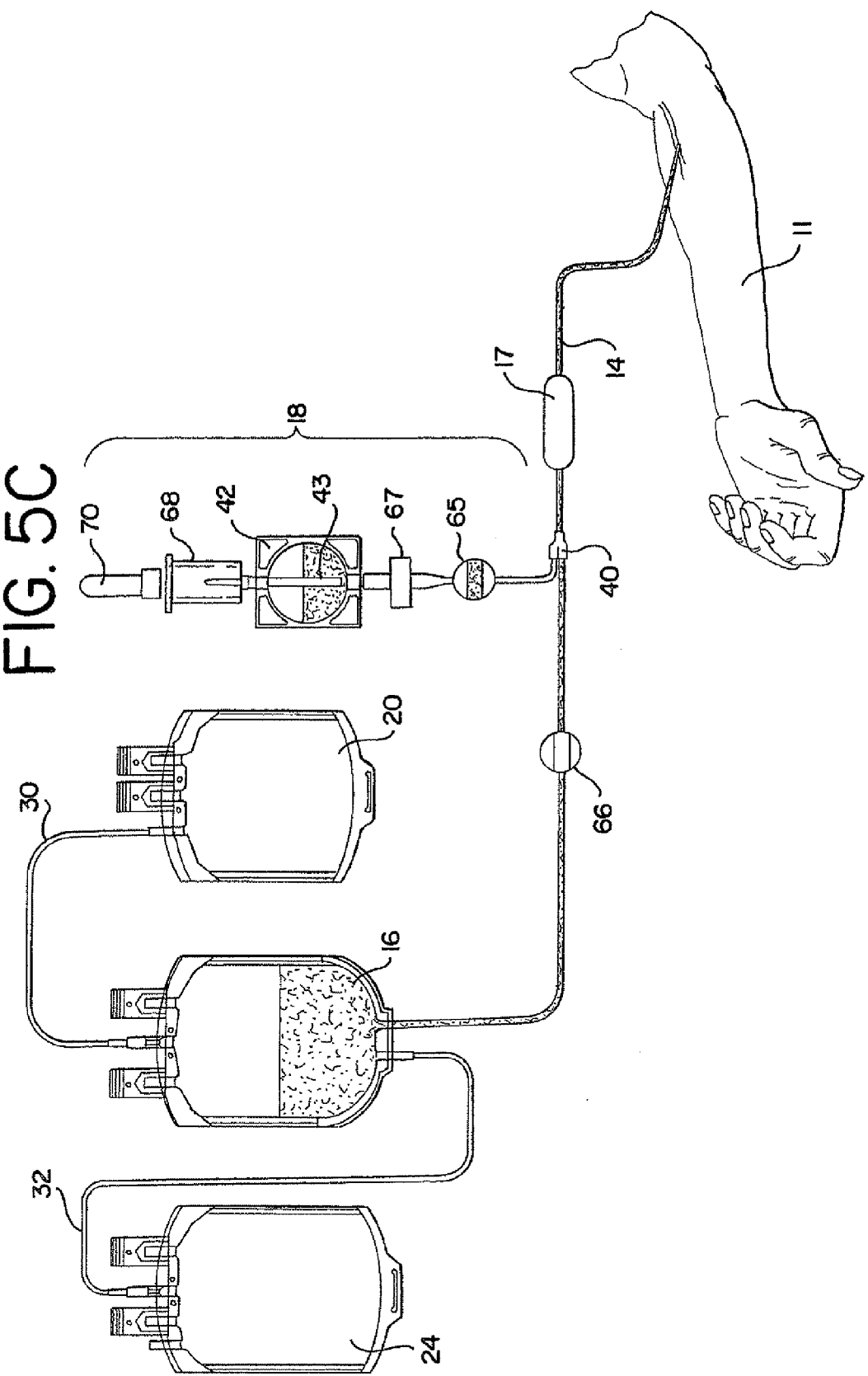

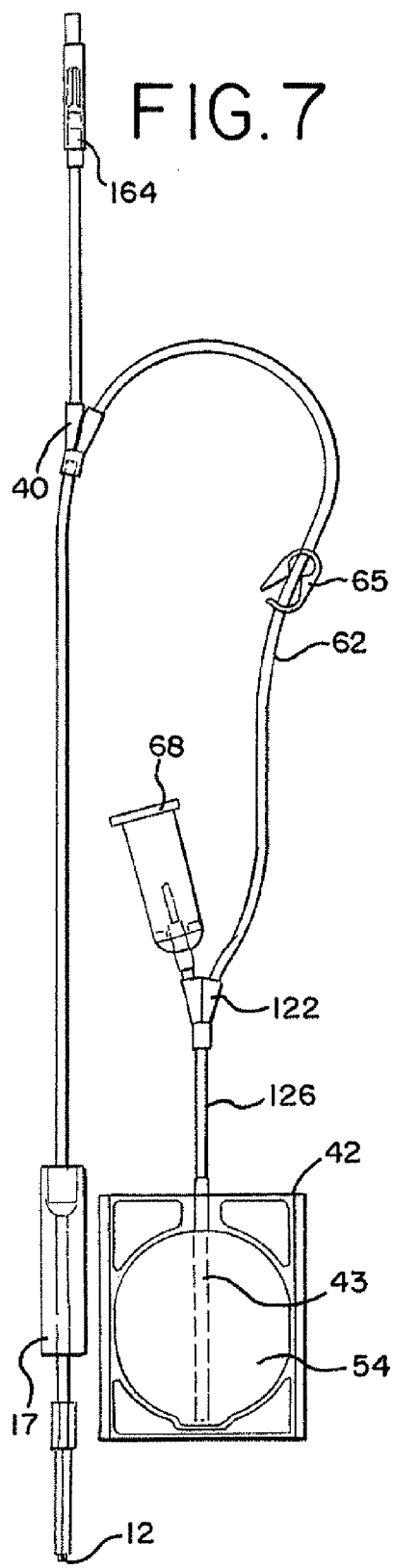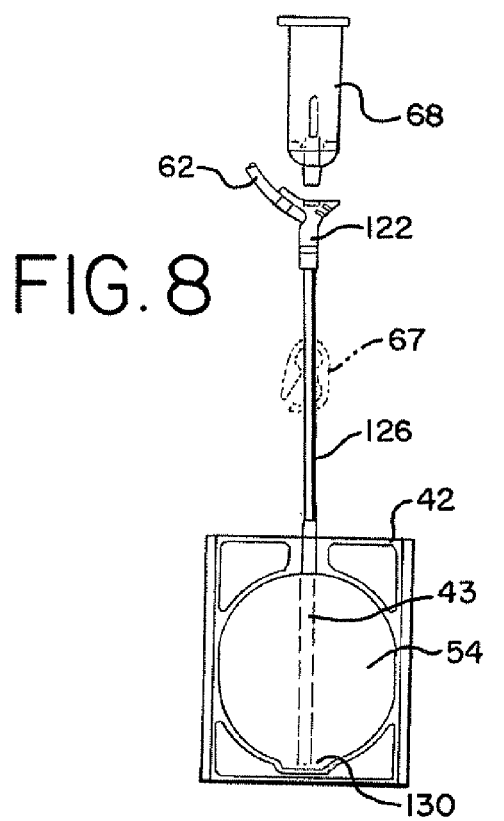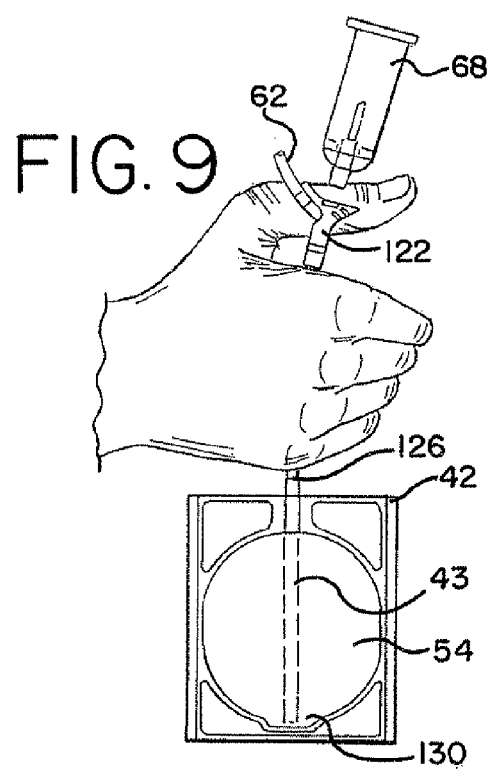

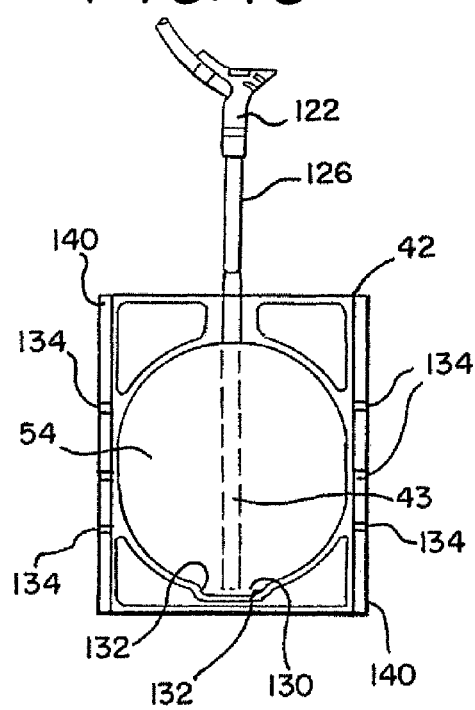
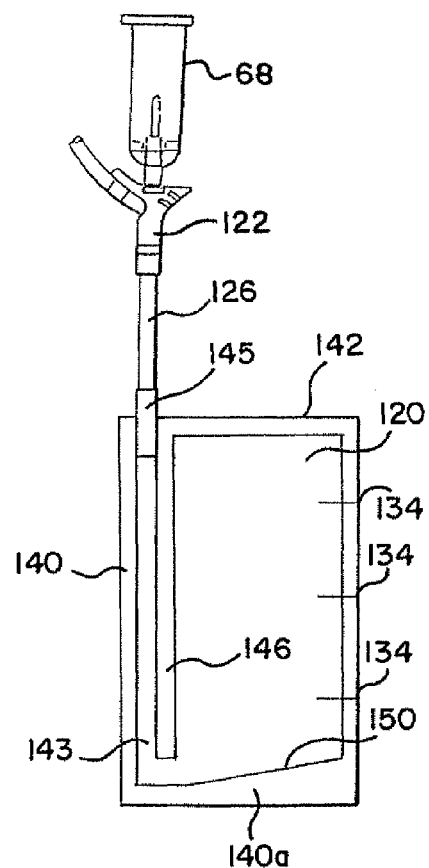
FIG. 13
FIG. 14

METHOD AND APPARATUS FOR BLOOD SAMPLING

CROSS-REFERENCE TO RELATED APPLICATIONS

This is a continuation-in-part of U.S. application Ser. No. 10/304,299, filed Nov. 26, 2002, now U.S. Pat. No. 7,044,941 which is a division of U.S. application Ser. No. 09/492,060, filed Jan. 27, 2000, now U.S. Pat. No. 6,520,948, which is a continuation-in-part of U.S. patent application Ser. No. 09/364,628 filed on Jul. 29, 1999, now U.S. Pat. No. 6,387,086, and which incorporates by reference each of the above-identified patents and/or applications.

BACKGROUND OF THE INVENTION

The administration of blood or blood components often plays a critical role in the emergency and/or long term treatment of patients. Blood or the individual components of blood (such as platelets, plasma, red blood cells, etc.) may be administered or transfused to patients to treat a variety of conditions. For example, blood may be administered to a patient to replace blood lost as a result of trauma, while individual blood components may be administered as part of a longer term treatment of patients suffering from cancer or certain blood related diseases. The blood or blood components administered to the patient come from blood previously collected from donors.

One of the most common blood collection techniques, and perhaps the most well-known, is the "manual" collection of whole blood from healthy donors. As commonly understood and as used herein, "manual" collection refers to a collection method where whole blood is allowed to drain from the donor and into a collection container without the use of external pumps or similar devices. This is in contrast to the so-called "automated" procedures where blood is withdrawn from a donor and further processed by an instrument that typically includes a processing or separation device and pumps for moving blood or blood components into and out of the device.

Regardless of whether the blood collection technique is manual or automated, withdrawing blood from the donor typically includes inserting a vein access device, such as a needle, into the donor's arm (and, more specifically, the donor's vein) and withdrawing blood from the donor through the needle. The "venipuncture" needle typically has attached to it, one end of a plastic tube that provides a flow path for the blood. The other end of the plastic tube terminates in one or more pre-attached plastic blood containers or bags for collecting the blood. The needle, tubing and containers make up a blood processing set which is pre-sterilized and disposed of after a single use.

In the manual technique, the collection container and plastic tubing may also include a volume of a liquid anticoagulant, while in the automated technique, a separate container of anticoagulant may be provided from which the anticoagulant is metered into the flow path and mixed with the incoming whole blood. In any event, anticoagulant is required because of the tendency of blood to clot and adhere to the walls of the plastic surfaces which it contacts.

An important consideration in any blood collection technique or system is ensuring that the system or set does not become contaminated by airborne bacteria or other foreign substances that may compromise the sterility of the system. Thus, the sterility of the above-described disposable blood processing set or system is maintained by minimizing exposure of the flow paths and interiors of the blood containers to the outside environment. Such systems are commonly referred to as "closed" systems.

After collection but prior to transfusion to a patient, the blood is typically tested for determining blood type and the presence of pathogens such as virus, bacteria and/or other foreign substances in the donor's blood. Typically, testing of the collected blood requires obtaining a sample of the blood from the blood donor at or near the time of collection.

One well-known technique of obtaining a blood sample is to simply withdraw or collect the blood remaining in the flow path of the disposable set after donation. This involves removing the needle from the donor, inserting the needle into a vacuum sealed sampling tube and allowing the blood from the flow path to drain into the tube. However, because there is a limited supply of blood remaining in the flow path, there may not be enough blood to provide enough of a sample to perform all of the required or desired testing. Accordingly, if a larger volume or numerous samples of blood are required, the technician obtaining the sample may continue draining the blood from the tubing, eventually withdrawing the collected anticoagulated blood from the collection container. Withdrawing blood from the collection container, however, may be less desirable in that it may expose the collected blood in the collection container to the outside environment. Withdrawing blood from the collection container for sampling also reduces the volume of available blood for later processing and transfusion.

An alternative to collecting anticoagulated blood from the collection container is to clamp off the flow path near the collection container and divert the blood being withdrawn from the donor to a collection (sampling) tube or tube of the type described above. This procedure typically employs a particular type of disposable tubing set having a pre-attached sampling site on the main flow path. Blood at or near the sampling site may be obtained by piercing the sampling site with a separately provided needle or other piercing device, and attaching a sampling tube thereto. To minimize the risk that the incoming blood (which is intended for later processing and transfusion) will be exposed to the outside environment, the sample is typically collected after completion of the blood donation.

Still another example of a blood sampling system is described in U.S. Pat. No. 5,167,656, which is assigned to the assignee of the present application. That patent describes a disposable tubing set wherein the flow path includes an enlarged sample collection portion. Blood for sampling is collected in the enlarged portion by clamping off the flow path near the collection container and allowing the enlarged tubing portion to fill with blood. Once the desired volume of blood for sampling is collected in the enlarged tubing portion, the needle is removed from the donor and the blood is transferred to a tube by piercing the cap of the tube with the needle and allowing the blood to drain into the sampling tube.

While these known techniques have generally worked satisfactorily, efforts continue to provide further improvements in the area of blood sampling. For example, as set forth above, the sample is typically obtained after the blood product (intended for further processing and transfusion) has been collected so as to preserve the sterility of the closed system. However, if the donation procedure must be terminated before completion, there may not be an opportunity to obtain a sample directly from the donor. Thus, it would be desirable to provide a sampling system in which blood samples can be obtained either before or after donation, but without the risk of compromising the sterility of the system and/or the collected blood product.

In addition, as discussed above, the use of vacuum-filled tubes or tubes is common in blood sampling processes. When such vacuum-filled tubes are used, there is the possibility that the suction may cause the tubing of the blood processing set to collapse and restrict blood flow. Of even greater concern, particularly in small-veined donors, is the possibility that the suction may cause the donor's vein to collapse. Thus, it would also be desirable to provide a sampling system where the risk of donor vein or tubing collapse is minimized.

It would also be desirable to provide a sampling system which is integrated with the blood collection set and requires few separate or external components.

Finally, where the sampling system includes a holder (with a piercing member) for receiving a sampling tube, it would also be desirable to provide a holder that is compact in size, easily sterilized and reduces the risk that the user will inadvertently come into contact with the sharpened tip of the piercing member within the holder.

SUMMARY OF THE INVENTION

In accordance with one aspect of the subject matter of the application, a biological fluid sampling system is disclosed. The system comprises a flexible plastic container comprised of two flat sheets melt sealed together substantially along their peripheries and defining an interior chamber. A sample access site is external to and spaced from the container. An internal flow path provides the only path for biological fluid flow into and from the interior chamber and communicates with the access site. The internal flow path extends substantially into and substantially across the entire distance of the interior chamber to allow for substantially complete drainage of the container.

BRIEF DESCRIPTION OF THE DRAWINGS

FIG. 1 is a plan view of a disposable blood collection or processing set including a sampling system;

FIG. 1A is a plan view of a portion of an alternative disposable blood collection or processing set including a sampling system;

FIG. 2B is a plan view of another variant of a disposable blood collection or processing set including a sampling system;

FIG. 2D is a plan view of another variant of a disposable blood collection or processing set including a sampling system embodying the present invention;

FIG. 3 is a perspective view of a sampling system;

FIG. 4 is a perspective view of the sampling system of FIG. 3 with an another embodiment of a holder;

FIG. 5A is a diagram showing one step in the method of obtaining a blood sample in accordance with the present invention;

FIG. 5C is a diagram showing the steps of isolating the blood sampling system from the remainder of the processing set and collecting blood in the collection container.

FIG. 7 is a partial, plan view of a blood collection and processing set with a sampling system embodying the present invention with a pre-attached sample tube holder;

FIG. 8 is a partial plan view of the set of FIG. 6;

FIG. 9 is a partial plan view of the set of FIG. 6 showing the preferred orientation of the sample container during sampling;

FIG. 13 is a plan view of one embodiment of the sample container of the present invention; and FIG. 14 is a plan view of an alternative embodiment of a sample container of the present invention.

DETAILED DESCRIPTION OF THE DRAWINGS

Figure 2A:
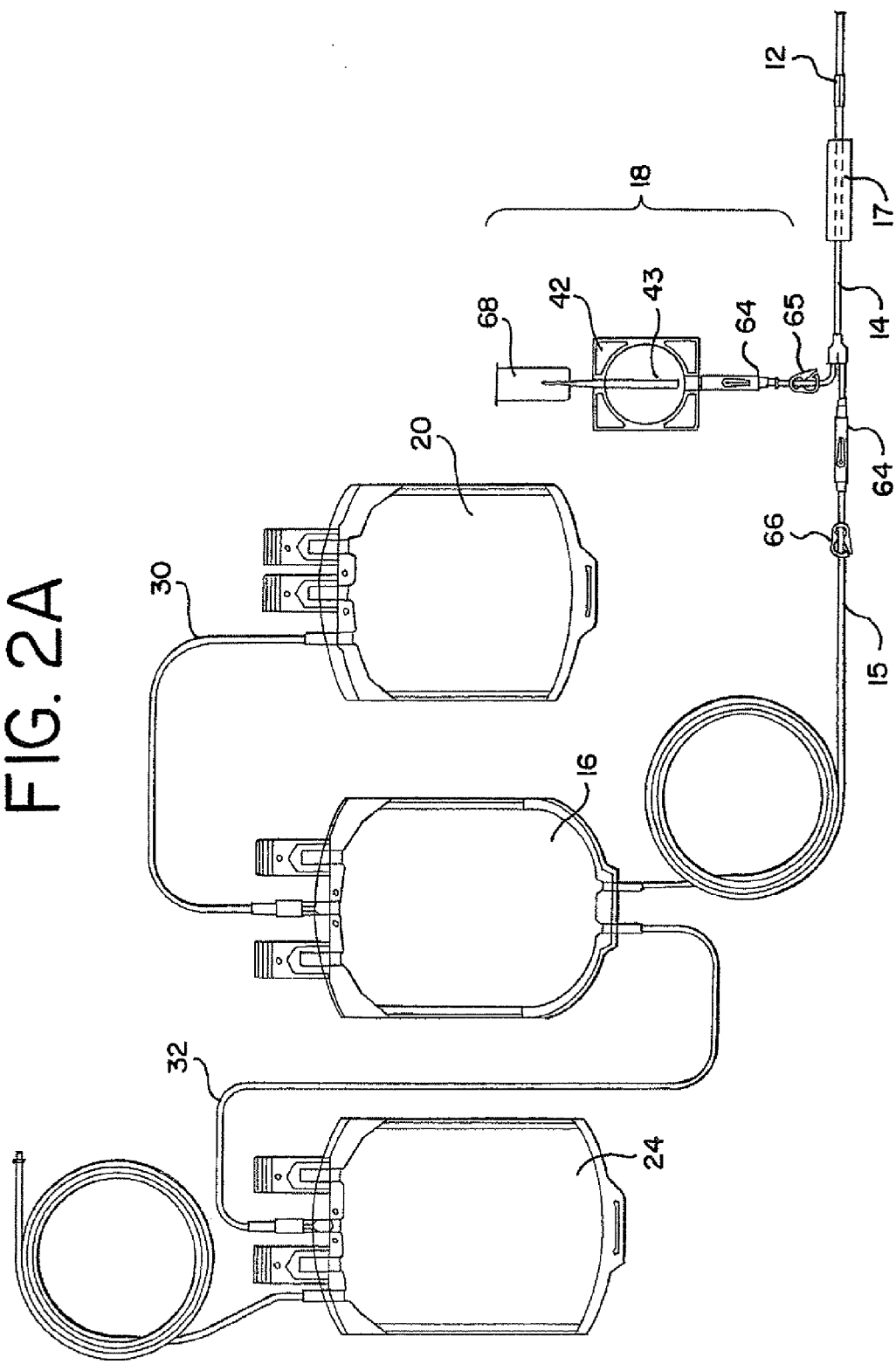
FIG. 2A is a plan view of another variant of a disposable blood collection or processing set including a sampling system.

Turning now to FIG. 1 of the drawings, the present invention may be embodied in a liquid flow conduit set such as a disposable processing set 10, which is particularly suitable for use in the manual collection of blood from a donor 11. The illustrated disposable set 10 may include a needle such as venipuncture needle 12, and plastic tubings 14 and 15 extending from needle 12 to a collection container such as a flexible plastic container 16. A needle protector 17 may also be provided for retraction and storage of needle 12 after use.

The blood processing set 10 may include a single blood collection container 16 or, more preferably, as shown in FIG. 1, may be a multiple blood container system including additional containers 20 and 24. In accordance with the present invention, disposable processing set 10 includes a sampling system 18, described in more detail below.

As set forth above, blood processing set 10 may include a primary container 16 and one or more integrally attached transfer containers 20 and 24. During use, primary container 16 (sometimes referred to as the donor bag) receives whole blood from the donor through integrally attached donor tubings 14 and 15 and venipuncture needle 12. Container 16 typically includes a suitable anticoagulant such as citrate phosphate dextrose (CPD), citrate phosphate dextrose adenine (CPDA) or acid citrate dextrose (ACD).

Containers 20 and 24 may be attached to primary container 16 by integrally attached transfer tubing 30 and 32. Containers 20 and 24 are provided to receive blood components such as, but not limited to, red blood cells and plasma that have been separated from whole blood. For example, collected whole blood in container 16 may be centrifuged to separate the blood into layers of such components. The heavier cellular components, such as red blood cells, settle to the bottom of the container 16 and the lighter, less dense components, such as plasma (with or without platelets), remain in the top layer. The components may then be separated by expressing the lighter components through transfer tubing 30 and into container 20. Likewise, the heavier components may be expressed through transfer tubing 32 to container 24. Such "top and bottom" separation techniques and disposable processing sets are well known and are available from Baxter Healthcare Corporation of Deerfield, Ill. under the name Optipac®.

Of course, it will be understood that the present invention is not limited to the processing sets shown in the figures and that processing sets having different container and tubing configurations are also within the scope of the present invention. For example, a multiple container system wherein tubing segments 30 and 32 are both attached to container 16 at or near the top of container 16 may also be used. Container 24 may include a volume of a preservative or storage solution which is introduced into container 16 and combined with separated red cells after plasma has been expressed to container 20. Such blood processing sets are also available from Baxter Healthcare Corporation.

Containers 16, 20 and 24 and associated tubing segments of processing set 10 are typically made from conventional and approved medical grade plastic materials. One such material may be polyvinyl chloride that includes a plasticizer such as, but not limited to, plasticizers selected from the family of citrate esters, which are described in U.S. Pat. Nos. 5,167,657, 5,100,401 and 5,026,347, all of which are incorporated by reference herein. Containers made from polyvinyl chloride plasticized with citrate ester or other plasticizers are available from Baxter Healthcare Corporation of Deerfield, Ill. Alternatively, and depending in part on the blood components to be stored, containers may be made from other materials such as polyolefin materials with or without plasticizer.

Turning now to the sampling system, as shown in FIG. 1, sampling system 18 may be integrally attached to the disposable processing set 10 at Y-connector 40. In general, and as shown in greater detail in FIG. 3, sampling system 18 may include a container 42 having an inlet port 46 and outlet port 50. Container 42 further includes an interior chamber 54 defined by walls 56 and 58 (FIG. 4) that are joined together in a facing arrangement. Walls 56 and 58 may be made from sheets of extruded plastic. Container 42 may be made by heat sealing together walls 56 and 58 or by any other method known to those of skill in the art. Preferably, walls 56 and 58 may joined together by radio frequency (RF) sealing the walls substantially along their peripheries. A bushing 47, (typically made of polyvinyl chloride) may be included at, for example, inlet port 46, and may also be RF sealed to walls 56 and 58.

Container 42 (or the walls 56 and 58) may typically be made of any conventional medical grade plastic material that is sterilizable by known sterilization techniques including autoclaving. One such preferred material is polyvinyl chloride with a plasticizer, such as a citrate ester (e.g. n-butyryltri-n-hexyl citrate), as substantially described above. Of course, other known plasticizers such as TEHTM and DEHP may also be used. In one example, the material used to make walls 56 and 58 may include approximately 70%, by weight, polyvinyl chloride and approximately 30%, by weight, plasticizer.

Container 42 may also include an internal flow path that extends substantially into the interior chamber 54 of container 42. In a preferred embodiment, the internal flow path may be defined by a plastic tube 43. As shown in FIGS. 3-4, in the preferred embodiment, one end of tube 43 is attached to container 42 and may provide outlet port 50. Preferably, tube 43 may be RF sealed to container walls 56 and 58. Tube 43 may be made of any typical medical grade material such as polyvinyl chloride with a plasticizer. Tube 43 extends substantially into interior chamber 54 and terminates near inlet port 46. Extending tube 43 substantially into interior chamber 54 assures that the end of tube 43 will reside within or near the liquid inside container 42, making it less likely that air will be present when liquid (such as blood) is withdrawn from container 42 into a sampling tube. Tube 43 also separates walls 56 and 58 to provide chamber 54 and assists in preventing walls 56 and 58 from collapsing during, for example, heat sterilization. As shown in FIG. 3, in a preferred embodiment, interior chamber 54 may be generally circular (i.e., have a generally circular profile). This may allow for more complete drainage of container 42 by eliminating corners where the blood may otherwise reside. In one embodiment, interior chamber 54 of container 42 may have a volume of approximately 20-100 ml and, more preferably, approximately 30-70 ml and, in some countries, a minimum volume of approximately 50 ml.

As further shown in FIG. 3, sampling device 18 may include tubing segment 62 attached to container 42 at inlet port 46. Tubing segment 62 may be attached to container 42 and, more specifically, bushing 47 by, for example, solvent bonding. The other end of tubing segment may be bonded to Y-connector 40. Tubing segments 62 may further include an openable barrier 64 such as a frangible cannula or connector of the type described in U.S. Pat. No. 5,330,464, assigned to the assignee of the present application and incorporated by reference herein. Barrier 64 preserves the sterility of the flow path defined by tubing segment 62. Flow restrictor clamps, such as Roberts-type clamps 65 and 66 (FIG. 1), on tubing segment 62 and tubing segment 15 may also be provided to allow for flow control through blood processing set 10 by the technician. In one embodiment, clamp 65 on tubing segment 62 may be a substantially irreversibly closeable clamp of the type described in WO 03/063945, which is incorporated herein by reference.

Sampling system 18 may further include a receptacle or holder 68 as shown in FIG. 3. As will be described in more detailed below, holder 68 is adapted to receive a blood sampling tube 70. Holder 68 may be attached to container 42 at outlet port 50 to provide an integrated system. In one embodiment, holder 68 includes distal luer end 69 which may be mated with and bonded to outlet port 50 prior to heat sterilization. More preferably, distal end port 69 may be bonded to tube 43. Subsequent heat sterilization forms a bond between the polycarbonate material of distal end 69 and, for example, tube 43. Of course, other ways of bonding holder 68 to container 42, such as solvent bonding, may also be used. Alternatively, holder 68 may be separately provided and attached to outlet port 50 at the time of use, or used to access an access site that communicates with container 42.

In one embodiment (shown in FIG. 3), holder 68 may have a central body portion 71, generally in the shape of a hollow cylinder. Holder 68 is open at its proximal end to allow for insertion of sampling tube 70. Holder 68 may be made of any plastic sterilizable material. Holders of the type generally discussed above are available from, for example, Becton-Dickinson Co. of Franklin Lakes, N.J.

Holder 68 may include a piercing member 74 as generally shown in FIG. 3 (or FIG. 4). Piercing member 74 may be a needle, cannula or other biocompatible device having a sharpened tip. As set forth above, piercing member 74 includes a piercing end 76. Piercing member 74 may be made of any material of sufficient strength such as metal or plastic. In addition, end 76 of piercing member 74 may be enclosed within a protective sheath 80. Protective sheath 80 may preferably be made of a flexible material, such as latex, which is capable of being penetrated by the tip of piercing member end 76. Also protective sheath 80 should be sufficiently resilient to return to its original shape (covering end 76) upon withdrawal of sampling tube 70. Holder may include a cap, such as a flip-cap, of the type shown and described in U.S. Patent Application Publication No. US 2004/0082899, which is incorporated herein by reference.

During a collection procedure, a sampling tube 70, as shown in FIG. 3, may be inserted into the interior of holder 68. As shown in FIGS. 3 and 4B, tube 70, which is typically a vacuum sealed tube, may itself include a piercable cap 84.

Such tubes are available from the Becton-Dickinson Co. of Franklin Lakes, N.J. and are sold under the trade name VACUTAINER®.

Figure 5B:
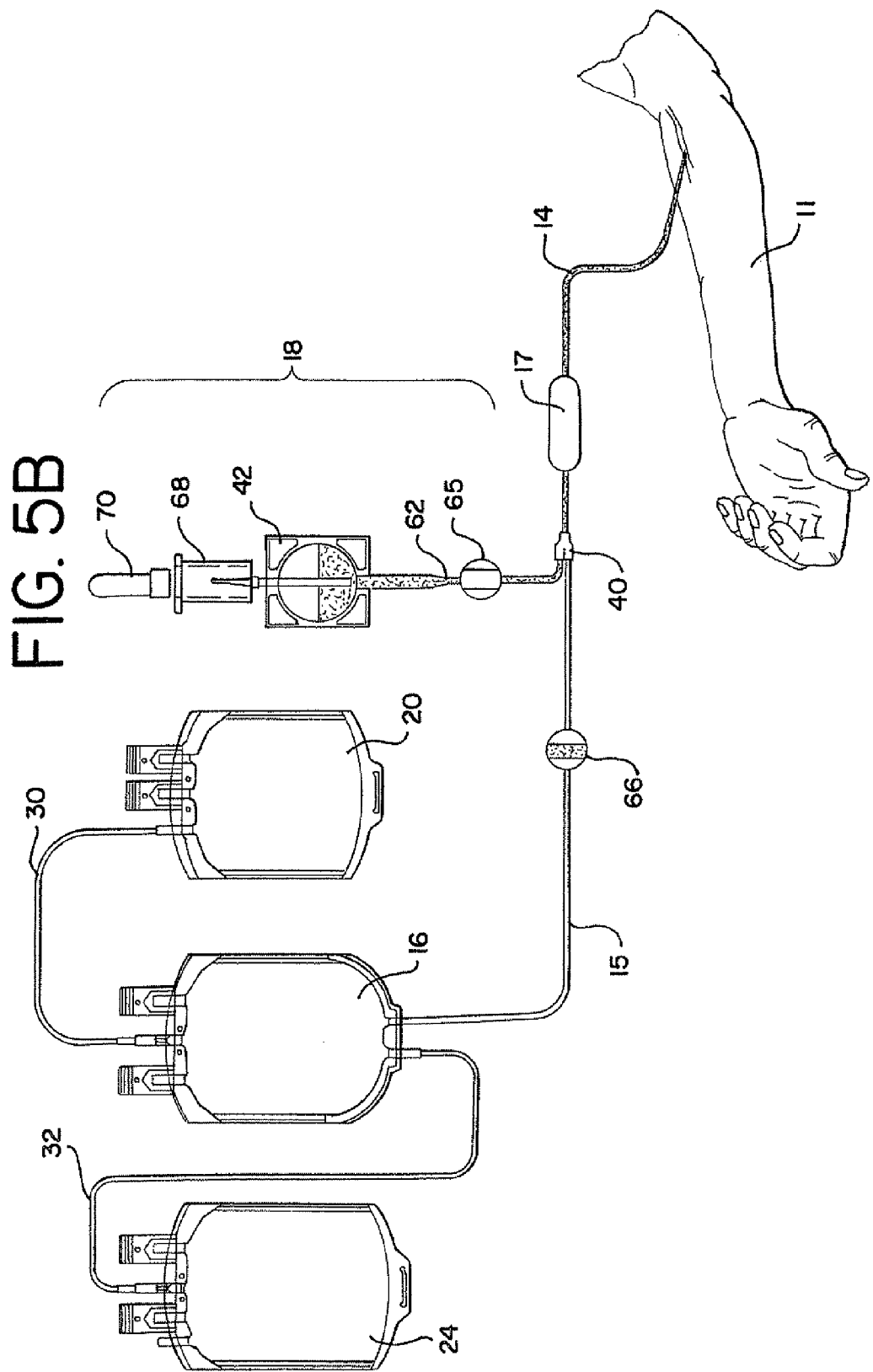
FIG. 5B is a diagram showing the step of filling a sample container with blood.

The method of collecting a blood sample from a donor during a blood donation using the blood processing system generally described above will now be described. In one embodiment, at the outset of the donation procedure, disposable processing set 10 may be provided with clamps 65 and 66 in a closed position, as shown in FIG. 5A. Next, optional frangible connector 64 is opened and needle 12 is inserted into the arm of the donor 11. As further shown in FIG. 5B, clamp 65 is opened and blood from the donor is allowed to flow into container or pouch 42. Alternatively, in some embodiments, clamp 65 may be opened prior to venipuncture.

Once a sufficient volume of blood for sampling has been collected, sampling system 18 may be isolated from the remainder of the processing set 10 by heat sealing tubing segment 62 in ways that are known to those of skill in the art. One device that may be used for sealing is the tubing sealing device known as the Hematron®, sold by Baxter Healthcare Corporation. Alternatively, line 62 may be sealed by a metal retaining clip or other means known to those of skill in the art. After isolation by seal 67, clamp 65 is closed and the clamp 66 is opened to allow blood flow into container 16 as shown in FIG. 5C. Of course, it will also be appreciated by those of skill in the art that in some embodiments, clamp 65 may be closed and clamp 66 or other flow control device (e.g., frangible 164 in FIGS. 6 and 7) may be opened (to allow blood flow into container 16) before heat sealing tubing segment 62.

Figure 5D:
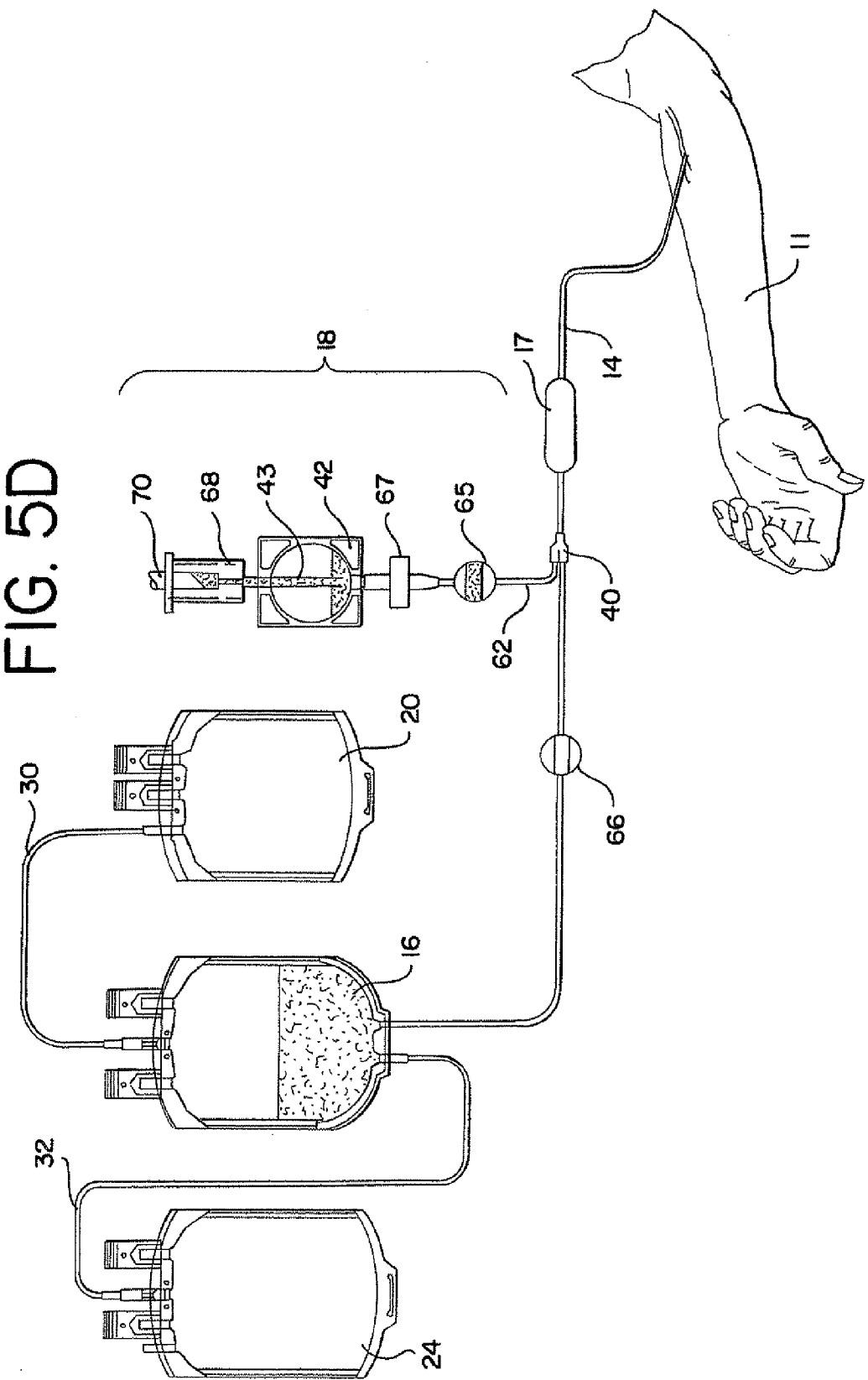
FIG. 5D is a diagram showing the step of withdrawing the blood sample from the sampling container and collecting it in a sampling tube (i.e., sampling).

In any event, once sampling system 18 has been isolated from the remainder of the blood processing set 10, blood collected in sample container 42 may be transferred to a sampling tube 70 as shown in FIG. 5D and in more detail in FIGS. 3 and 4C. Sampling tube 70 is inserted into the interior of holder 68 so that cap 84 of tube 70 is pierced by the piercing end 76 of piercing member 74, as generally shown in FIG. 4B. As shown in FIGS. 3 and 4, it is preferred that sampling tube 70 be introduced into holder 68 in an inverted position so that blood flows up into tube 70. Applicants have discovered that such blood flow results in less hemolysis of red blood cells as compared to other collection techniques where the blood is allowed to drip into an upright tube.

Finally, turning briefly to FIGS. 1A and 2A-2D, the blood processing sets shown therein are variants of the processing set 10 of FIG. 1. While the sampling systems 18 shown in these embodiments are similar to the sampling system described above, the processing sets differ, in general, in the presence and location of openable barriers 64, the orientation of certain components, the introduction and withdrawal of blood into and from sample container 42 and the like. For example, the blood processing set shown in FIG. 1A is virtually identical to the set of FIG. 1 with the exception that Y-connector 40 is oriented in the opposite direction (which may be desirable for packaging purposes).

In FIG. 2A, an additional openable barrier 64 of the type described above may be included on line 15. Inclusion of barrier 64 on line 14 may prevent additional anticoagulant from entering line 14 distal to Y-connector 40. A similar but alternative embodiment is shown in FIG. 2B where an openable barrier 64a (such as a polyvinyl chloride frangible cannula) is located near the inlet port of container 16. In these embodiments, barrier 64 or 64A would be opened just prior to collection of blood in container 16.

Figure 2C:
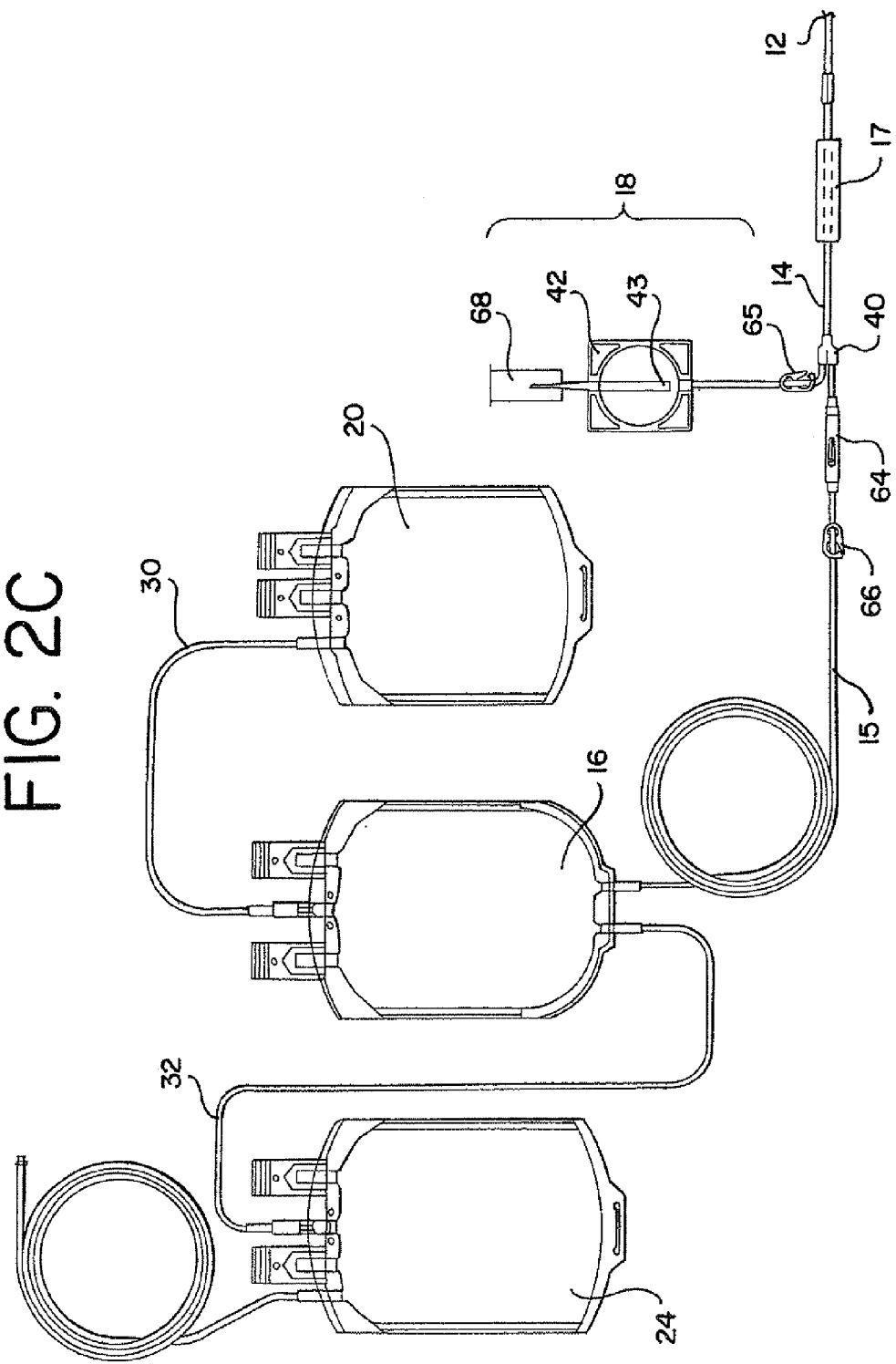
FIG. 2C is a plan view of another variant of a disposable blood collection or processing set including a sampling system.

In another embodiment, shown in FIG. 2C, an openable barrier 64 may be included on line 14, but not on line 62. In this embodiment, holder 68 preserves the sterility of the system. Finally, as shown in FIG. 2D, a Y-site of the type described in U.S. Pat. No. 5,372,143, which is incorporated by reference herein, may be used in combination with the sampling system 18 of the present invention.

More specifically, sampling system 18, shown in FIG. 2D, includes a sample container or pouch 42, tube 43 that extends substantially into the interior chamber 54 of pouch 42, and an access site 122 external to container 42 through which blood from the donor is introduced into chamber 54. Chamber 54 is accessible by sample tube holder 68 through access site 122 and tube 43, as described, for example, in U.S. Pat. No. 5,372,143 (previously incorporated by reference).

Figure 6:
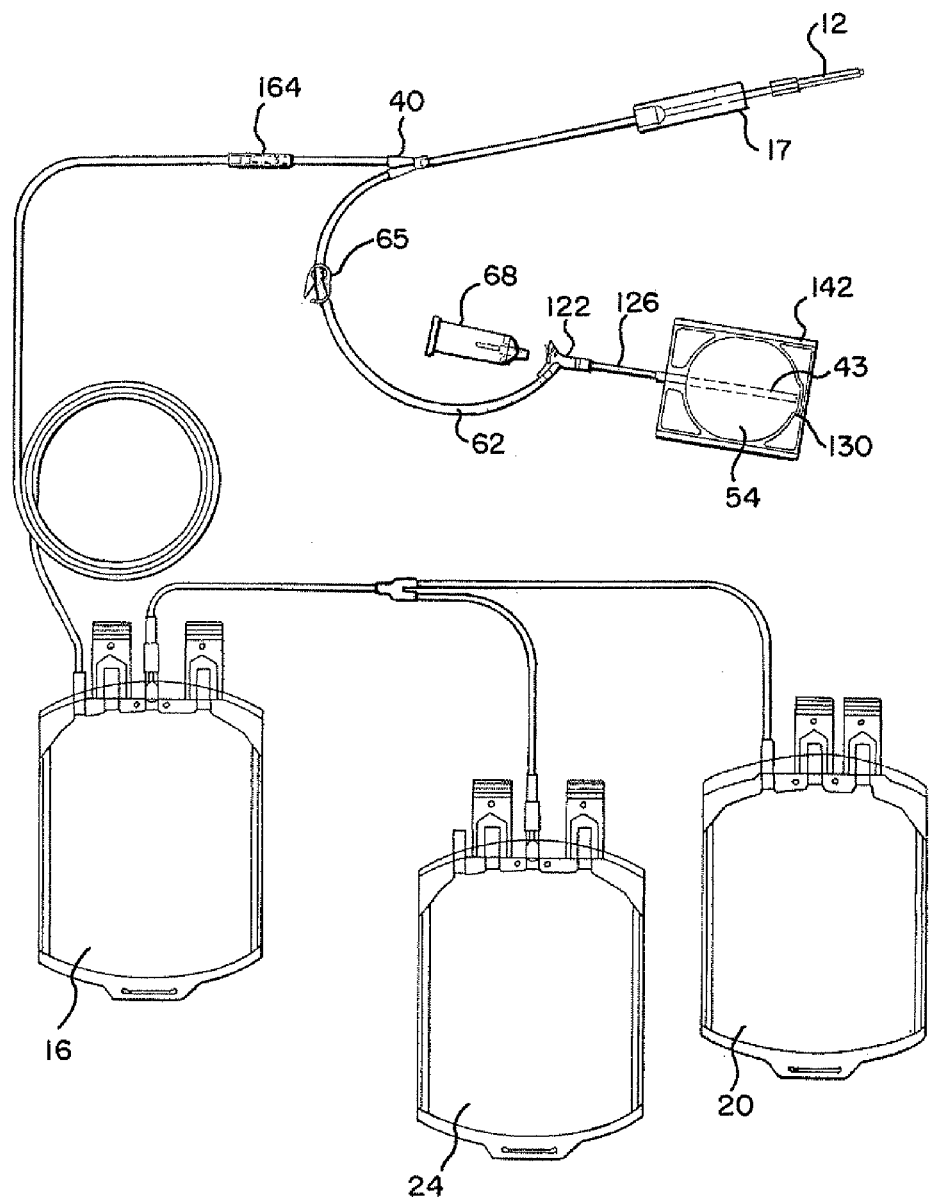
FIG. 6 is a plan view of another version of a blood collection and processing set with a sampling system embodying the present invention.

The sampling systems shown in FIGS. 6 and 7 are, in many respects, similar to the sampling system 18 of FIG. 2D, with some exceptions. In the embodiments of FIGS. 6 and 7, access site 122 is spaced a pre-selected distance from container 42. In the embodiment of FIG. 6, the spacing is provided by intermediate tube 126, although it will be appreciated by those of skill in the art that the spacing can also be provided by extending the length of tube 43. In a preferred embodiment, one end of tube 126 is joined to access site 122, and the other end is joined to tube 43. Tube 126 may be joined to access site 126 and tube 43 in ways well known to those skilled in the art, such as, but not limited to, solvent bonding. Spacing access site 122 from container 42 provides the user greater flexibility in orienting container 42 in a desired position relative to the access site 122 and sample tube holder 68 when performing the actual collection of blood in vacuum sealed tubes 70. Providing an access site spaced from the container allows the user to comfortably grasp tube 126 and/or access site 122 and orient the pouch 42, such that it hangs down from access site 122 as shown, for example, in FIG. 9. In this preferred orientation, tube 43 is substantially vertically disposed with its distal end residing in the reservoir of collected blood and away from air in the container. In that regard, it is preferred that access site 122 be spaced a sufficient distance from container 42 to allow the user to grasp the tube as also shown in FIG. 9. A tubing length that is too short may not provide enough room for the user to comfortably grasp access site 122 and/or tube 126 and still orient container 42 in the preferred position. On the other hand, excessive lengths of tubing separating access site 122 and container 42 also may not be desirable because they will provide too much space for air and are less compact for packaging purposes. A preferred distance between access site 122 and container 42 may be anywhere between 1 and 5 inches and, more preferably, between about 2 and 3 inches.

Another advantage of spacing access site 122 a sufficient distance from container 42 along the flow path between the two (i.e., by either intermediate tube 126 or an extended tube 43) is that it provides the user with the ability to stop the flow from chamber 54 to access site 122 during the sampling process. Stopping the flow to access site 122 may be desirable where, for example, holder 68 fails or is blocked, requiring attachment of a new holder 68 (access device). Thus, the distance between access site 122 and container 42 should be sufficient to accommodate a clamp (such as clamp 65 shown in phantom lines in FIG. 8) or other flow control device.

FIG. 7 is, in many respects, identical to the embodiment shown in FIG. 6, with the one exception that holder 68 is pre-attached to access site 122 adapted for receiving the luer end 69 of holder 68. Holder 68 may be pre-attached to a port of access site 122 in ways previously described, such as, but not limited to, adhesion bonding caused by the applied heat of sterilization or solvent bonding.

In contrast to the embodiments of FIGS. 1, 2A, 2B, and 2C, in the embodiments of FIGS. 2D, 6 and 7, the flow path that extends substantially into interior chamber 54 of pouch 42 serves the dual function of a blood entry flow path and a blood withdrawal flow path. In fact, the flow path shown as tube 43 in FIGS. 2D, 6 and 7, or internal flow passageway 143 in FIG. 14, provides the only access or flow path for the blood entering and exiting chamber 54.

Figure 10:
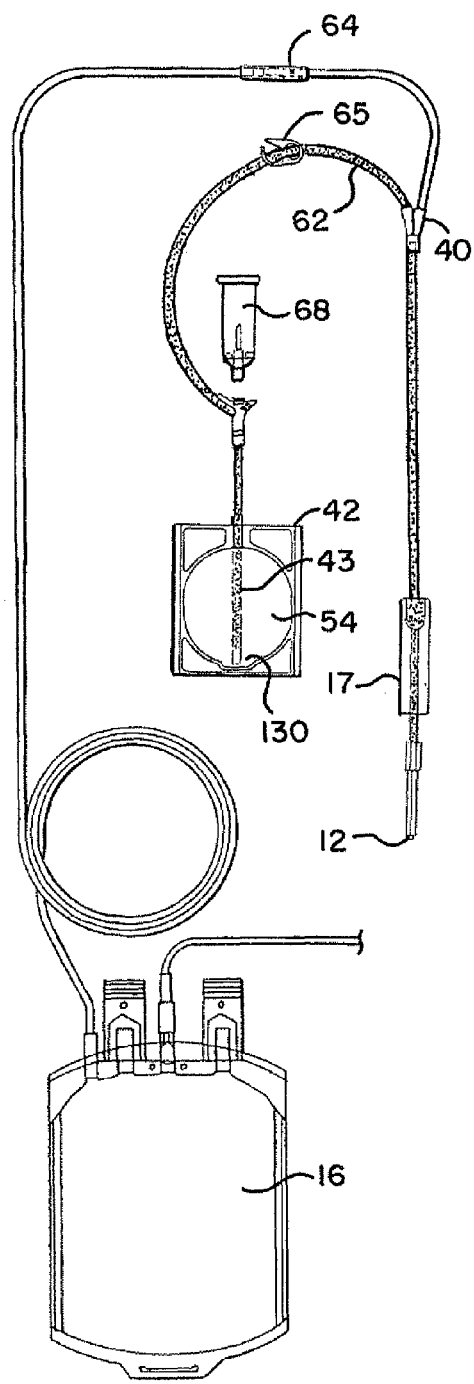
FIG. 10 is a plan view of the sample container filling step in the method of the present invention.

For example, with the clamp 66 (in FIG. 2D), or frangible barrier 64 (in FIGS. 6 and 7) closed, the venipuncture is made, and clamp 65 is opened. A portion of the blood from the donor flows into chamber 54 through tube 43, as best seen in FIG. 10. Once the sample container 42 is filled to the desired level, clamp 65 is closed, and the main collection is allowed to proceed (by opening, i.e., breaking frangible member 164), as discussed above and shown in FIG. 11. Line 62 may further be sealed by RF sealing or metal clips. At the time of sampling, i.e., collecting blood samples in vacuum sealed tubes 70, blood flows from chamber 120 through tube 43, through holder 68, to vacuum sample tube 70, as shown in FIG. 12.

Allowing tube 43 to serve as both the flow path for blood entering the container and the flow path for blood exiting the container provides advantages in addition to the benefits provided by tube 43 previously discussed (i.e., providing substantially complete drainage and preventing wall collapse during sterilization). By providing tube 43 for both blood entry and blood withdrawal, the sampling systems shown in FIGS. 2D and 6 and 7 ensure that air will not be introduced into the first vacuum sealed sample tube used in the sampling process, and that a full sample can be collected.

In other sampling systems and sampling operations for collecting a plurality of sample tubes that utilize a sample pouch, and separate access ports for blood introduction and blood withdrawal from the sample pouch, it is common for the first of the plurality of sample tubes to be underfilled. This is because resident air in the head space of the sample pouch and/or associated tubing is suctioned into the sample tube ahead of the blood. Such underfilled tubes may not be useable for sampling. In addition, introducing air into the sample tube may lead to hemolysis in the blood sample. Users of these systems have tried to overcome this problem by inverting the sample pouch to avoid collecting air, or by accessing the sample pouch from below or from the side of the sample pouch. Having to turn or otherwise manipulate the sample pouch, or access it from a position other than the top of the pouch can be awkward, burdensome and, in the end, unsatisfactory from the standpoint of the user.

Figure 11:
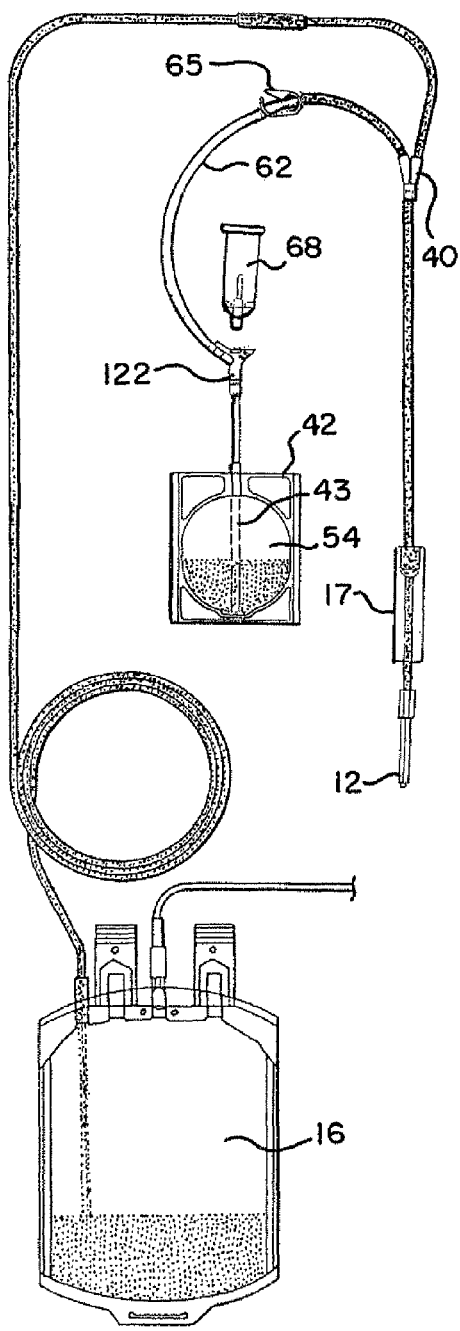
FIG. 11 is a plan view of a later blood collection step in the method of the present invention.
Figure 12:
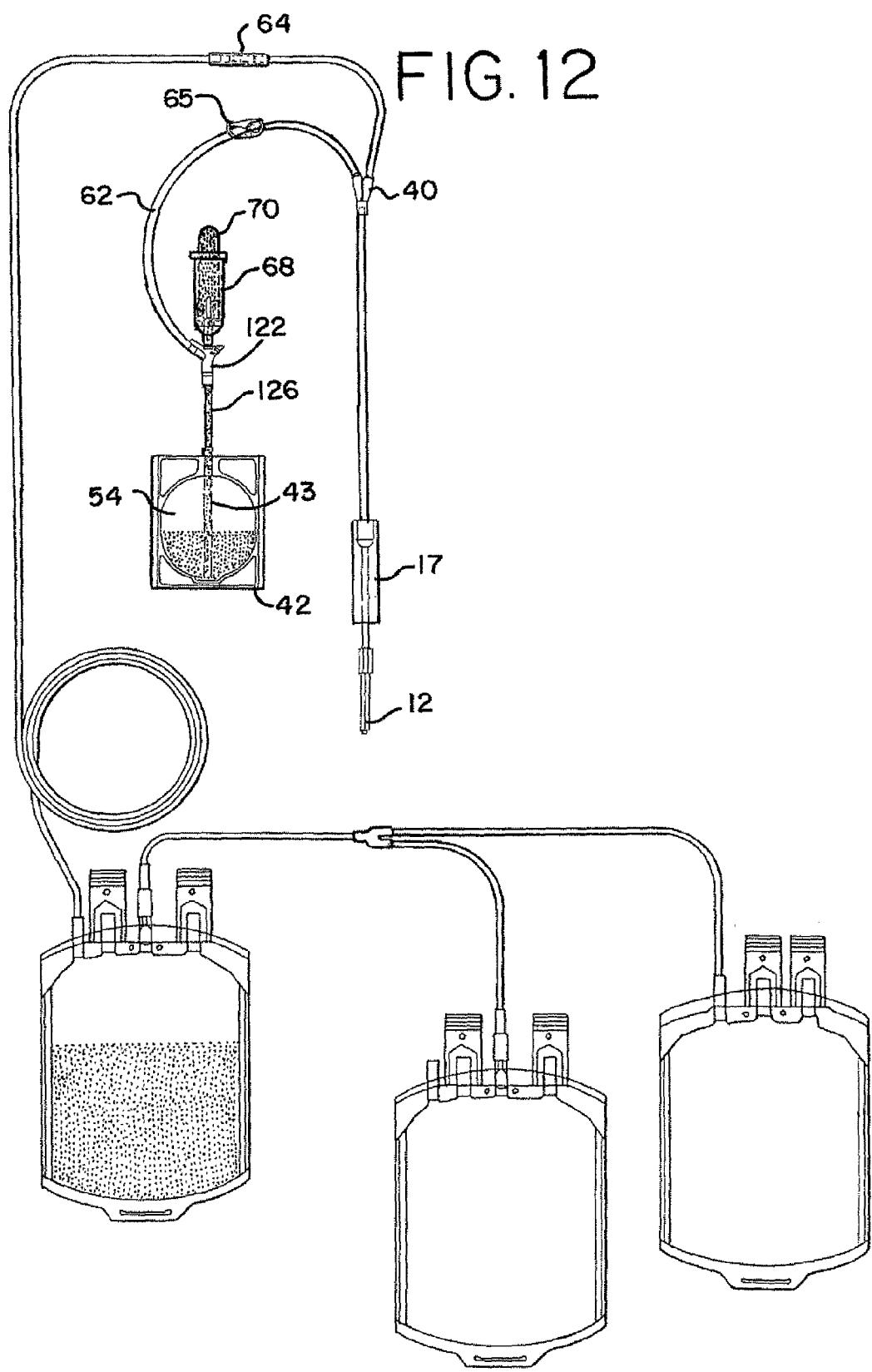
FIG. 12 is a plan view of the sample tube filling step in the method of the present invention.

In accordance with the present invention, air in the head space of container 42 is bypassed by tube 43, which extends substantially into the interior chamber 54 and, therefore, into the reservoir of collected blood as seen, for example, in FIG. 11. As for air that may reside in tube 43, any such resident air is displaced from tube 43 and into chamber 54 by incoming blood. During the initial draw of blood into container 42, the initial flow of blood pushes any air residing in tube 43 into chamber 54. As a result, tube 43 is substantially free of air. Thus, the first or initial sample tube 70 (i.e., the first aliquot or sample of blood to be removed from the sample pouch), inserted into holder 68 will substantially receive blood from the sample pouch, and not resident air from tube 43. This way, an underfilled first sample tube is avoided and the initial and subsequent sample tubes may be substantially free of excess air and be filled with a desired amount of blood. Avoidance of air also reduces the risk of hemolysis.

As shown in FIG. 13, container 42, and more specifically, chamber 54 of container 42, may be shaped to provide a well 130 near the base of chamber 54. Well 130 provides a funneling effect for blood in chamber 54, further ensuring that as much of the blood for sampling can be drained from container 42. As shown in FIG. 13, and as previously discussed, tube 43 extends substantially into the interior chamber of container 42. It is preferred that the distal end of tube 43 extend into the well 130. By extending the distal end of tube 43 into the well 130, drainage of blood from the container is improved. In addition, the sides 132 of well 30 also assist in retaining the distal end of tube 43 within well 130.

Container 42 may also include embossed, printed, or otherwise marked gradations along the side peripheral sealed edge of container 42. Embossed indicia may be provided at the time of sealing together container walls. The indicia or gradations 134 provide the user with a visual indication of the volume of blood for sampling. Indicia 134 for indicating the volume within the sample pouch are also shown in the container of FIG. 14 described below.

FIG. 14 shows an alternative embodiment of a sample container 142 with a flow path through which blood is introduced into chamber 120 and through which blood is withdrawn during sampling. In FIG. 14, container 142 includes two oppositely facing walls sealed together substantially along their peripheries by peripheral seal 140. An opening is provided through which blood is introduced and withdrawn. The opening may be a short length of plastic tubing (sealed to the facing walls) that provides a port 145 to which tube 126 may be attached to provide flow communication between access site 122 and flow path 143. Alternatively, tube 126 may have one end attached to access site 122 and its other end sealed to container 142.

As shown in FIG. 14, internal flow path 143 extends substantially into interior chamber 120. Internal flow path 143 may be defined by a portion of peripheral seal 140 and an interior seal 146 spaced from seal 140. Distal end 148 of interior seal 146 extends to point spaced from bottom peripheral seal 140*a*.

Interior chamber 120 of pouch 142 shown in FIG. 14 may include a sloped bottom 150 formed by bottom seal 140*a* to direct blood toward the distal end of internal flow path 143, thereby improving drainage from pouch 142 of FIG. 14. The walls of container 142 may be made of a plastic material that will not stick together during sterilization and/or container 142 may be provided with ribs or other means (that will be known to those skilled in the art) to prevent sticking of the walls during sterilization.

Whether the sample container is provided with a tube (e.g., tube 43) or other flow path (e.g., internal flow path 143), because the entry and withdrawal flow paths are one in the same, elimination of excess air from the vacuum sample tube can be accomplished without inversion of the sample container 42 (or 142) and without having to access the sample container from a location other than the top of the container.

The disposable processing set and sampling system of the present invention provide many benefits. One benefit is that a blood sample may be obtained prior to the donation while still preserving the sterility of flow path between the donor and collection container. Specifically, as described above, a blood sample may be collected in container 42 (or 142), which container may then be isolated from the remainder of the system (by, for example, sealing or clipping). Once container 42 has been isolated, a sampling tube may be introduced into the holder of the sampling system without the risk that bacteria or other foreign substances on the tube will contaminate the rest of the blood processing set, including flow path 14.

Another advantage is that blood samples can be collected without the introduction of excess air into the vacuum sample tube, making each collected sample, including the initial sample, useable for sampling and less likely to result in hemolysis of the blood cells caused by air.

An advantage of pre-donation sampling is that bacteria or foreign substances that may be present on the donor's skin will not be transmitted to collection container 16, but will be diverted to sampling container 42.

Another advantage of pre-donation sampling is that it allows for collection of sample for testing, even if the donation is not completed.

Another advantage of pre-donation sampling is that it may provide a more accurate profile of the donor's blood, particularly regarding the hemoglobin level of the donor. For example, during donation, the loss of blood volume in the donor is compensated by plasma. This compensation by plasma typically lowers the hematocrit of the donor's blood. If the sample is taken after donation, the donor hematocrit may be lower (by possibly as much as 0.5 g/dL) than it otherwise would be if the sample is collected prior to donation.

The present invention provides additional advantages, whether used for pre-donation or post-donation sampling. One advantage is the reduced risk of tubing or donor vein collapse as described above. Container 42 acts as a buffer between the sampling tube and tube or vein. Thus, any suction forces generated by introduction of the vacuum sealed tube will be absorbed by the container 42 and not tube or donor vein.

Of course, there may be other advantages of the present system not discussed herein which will be apparent to those of skill in the art.

The present invention has been described in accordance with the preferred embodiments. However, it will be understood that minor variations to the embodiments shown herein may be made without departing from the present invention which is specifically set forth in the appended claims.

That which is claimed:

1. A biological fluid sampling system comprising:
   a flexible plastic container comprised of two flat sheets melt sealed together substantially along their peripheries and defining an interior chamber;
   a sample access site external to and spaced from said container;
   an internal flow path providing the only path for biological fluid flow into and from said interior chamber, said internal flow path communicating with said access site;
   said internal flow path extending substantially into and substantially across the entire distance of the interior chamber to allow for substantially complete drainage of the container.

2. The sampling system of claim 1 further comprising an intermediate tube defining a flow path with one end of said tube directly communicating with said sample access site and the other end directly communicating with said internal flow path.

3. The sampling system of claim 1 wherein said interior chamber has a generally circular profile.

4. The sampling system of claim 1 wherein said interior chamber includes a fluid receiving well.

5. The sampling system of claim 4 wherein the distal end of said internal flow path extends substantially into said interior chamber, said internal flow path having a distal open end terminating within said well.

6. The sampling system of claim 1 wherein, at least one of said flat sheets is generally translucent and includes indicia thereon for indicating the volume of fluid within said chamber.

7. The sampling system of claim 1 wherein said internal flow path is defined by a plastic tube that extends substantially into said chamber interior.

8. The sampling system of claim 1 wherein said internal flow path is defined by an interior seal in said plastic bag.

9. The sampling system of claim 1 wherein said access site is adapted to receive a holder for a vacuum tube.

10. The sampling system of claim 9 further comprising a holder for receiving a vacuum tube.

* * * * *